United States Patent [19]

Taylor et al.

[11] Patent Number: 4,950,680

[45] Date of Patent: * Aug. 21, 1990

[54] METHOD AND COMPOSITIONS FOR INHIBITION OF TUMOR CELL INDUCED PLATELET AGGREGATION

[75] Inventors: John D. Taylor, Detroit; Kenneth V. Honn, Grosse Pointe Woods, both of Mich.

[73] Assignee: Board of Governors of Wayne State University, Detroit, Mich.

[*] Notice: The portion of the term of this patent subsequent to Sep. 1, 2004 has been disclaimed.

[21] Appl. No.: 661,953

[22] Filed: Oct. 17, 1984

Related U.S. Application Data

[63] Continuation-in-part of Ser. No. 480,704, Mar. 31, 1983, Pat. No. 4,690,935.

[51] Int. Cl.$^5$ .................... H61K 31/44; H61K 31/36
[52] U.S. Cl. .................................. 514/356; 514/465
[58] Field of Search ............................... 514/356, 465

[56] References Cited

PUBLICATIONS

Gordon, J. L. In: Platelets in Biology and Pathology–2 (J. L. Gordon, ed) Elsevier North Holland Biomedical Press, Amsterdam pp. 2–7 (1981).
Weiss, H. J. In: Platelets: Pathophysiology and Antiplatelet Drug Therapy. Alan R. Liss, Inc., New York pp. 13–17, 1982.
Jamieson, G. A., et al., In: Interaction of Platelets and Tumor Cells. Alan R. Liss, Inc., New York, pp. 405–413.
Gasic, G. J., et al., Int. J. Cancer 11:704–718, 1973.
Hara, H., et al., Cancer Res. 40:1217–1222, 1980.
Bastida, E., et al., Nature 291:661–662, 1981.
Gasic, G. J., et al., Proc. Natl. Acad. Sci. USA 61:46–52, 1968.
Honn, K. V., et al., Science 212:1270–1272, 1981.
Menter, D., et al., In: Prostaglandins and Cancer. First Intl. Conf. pp. 809–813, 1982.
Shaw, J. O. et al. Biochim. Biophys. Acta 714:492–499, 1982.
Imai, A., et al., Biochem. Biophys. Res. Commun. 108:(2)752–759, 1982.
Gerrard, J. M., et al., In: Platelets in Biology and Pathology—2 J. L. Gordon, ed., North Holland Biomedical Press, Amsterdam, pp. 407–436, 1981.
Rittenhouse-Simmons, S. J. Biol. Chem. 256:(9)4155, 1981.
Shukla, S. D. Life Sciences 30:1323–1335, 1982.
Serhan, C. N., et al., J. Biol. Chem. 257:(9) 4746–4752, 1982.
Gorman, R. R. Fed. Proc. 38:(1)83–88, 1979.
Parise, L. V., et al., J. Pharm. Expotl. Therap. 222:(1)276–281, 1982.
Vargaftig, B. B., et al., Biochem. Pharmacol. 30 263–271 (1981).
Hamberg, M., et al., Proc. Natl. Acad. Sci. USA 72:2994, 1975.
Heptinstall, S., et al., Thromb. Res. 20:219, 1980.
Moncada, S., et al., Nature 263:663, 1976.
Moncada, S., et al., In:Biochemical Aspects of Prostaglandins and Thromboxanes, (Eds. N. Kharasch and J. Fried), p. 155. Academic Press, New York, 1977.
Mullane, K. M., et al. Eur. J. Pharmacol. 54:217, 1979.
Moncada, S., et al., Prostaglandins. 12:715, 1971.
Szczeklik, A., et al., J. Pharmacol. Res. Commun. 10:545, 1978.
Gastpar, H., J. Medicine 8(2):103–114, 1977.
Bastida, E., et al., Cancer Res. 42:4348–4352, 1982.
Paschen, W., et al., P. Blut 38:17–24, 1979.

(List continued on next page.)

*Primary Examiner*—Jerome D. Goldberg
*Attorney, Agent, or Firm*—Ian C. McLeod

[57] ABSTRACT

Compositions and a method for inhibiting tumor cell induced platelet aggregation are described. Platelet aggregation by tumor cells is part of the metastatic cascade which is interrupted according to the present invention. The compounds include a mixture of at least two members of the group including a calcium channel blocker, a prostacyclin, a thromboxane synthase inhibitor and a phosphodiesterase inhibitor. All of the compounds utilized have an affect on calcium ion which controls platelet aggregation.

8 Claims, 12 Drawing Sheets

OTHER PUBLICATIONS

Honn, K. V., et al., Acta Clinica Belgica, in press, 1983.
Honn, K. V., et al., Biochem. Pharm., in press, 1983.
Owen, N. E., et al. Am. J. Physiol. 239:483–488, 1980.
Schumunk, G. A. et al., Res. Commun. Chem. Path. and Pharm. 35:(2) 179–187, 1982.
Owen, N. E. et al., Am. J. Physiol. 241:613–619, 1981.
Menter, et al., Cancer Research, 44, 450–456, 1984.
Honn, K., et al., Clinical and Exp. Metastasis 1:103–114 (1983).
Fleckenstein A., An. Rev. Pharmacol. Toxicol. 17:149–166 (1977).
Murphy KMM, Gould RJ, Largent BL and Snyder SH. Proc. Natl. Acad. Sci. USA 80:860–864, (1983).
Nayler WG and Grinwald P. Fed. Proc. Fed. Am. Soc. Exp. Biol. 40:2855–2861, 1981).
Lee KS and Tsien RW. Nature (London) 302:790–794, (1983).
Mustard et al., Br. J. Haemotology, 1972, 22:193–204.
Exptl. Cell Res. 13:341–347 (1957), Phillips.
Anal. Biochem. 98:112–115, 1979, Grant.
Diglio, C. A., Grammas, P., Giacomelli, F. and Wiener, Lab. Investigations, vol. 46, No. 6, p. 554 (1982).

WALKER 256 CARCINOSARCOMA RAT PLATELETS

B 16 AMELANOTIC MELANOMA

FIG. 5 TUMOR CELL INDUCED PLATELET AGGREGATION
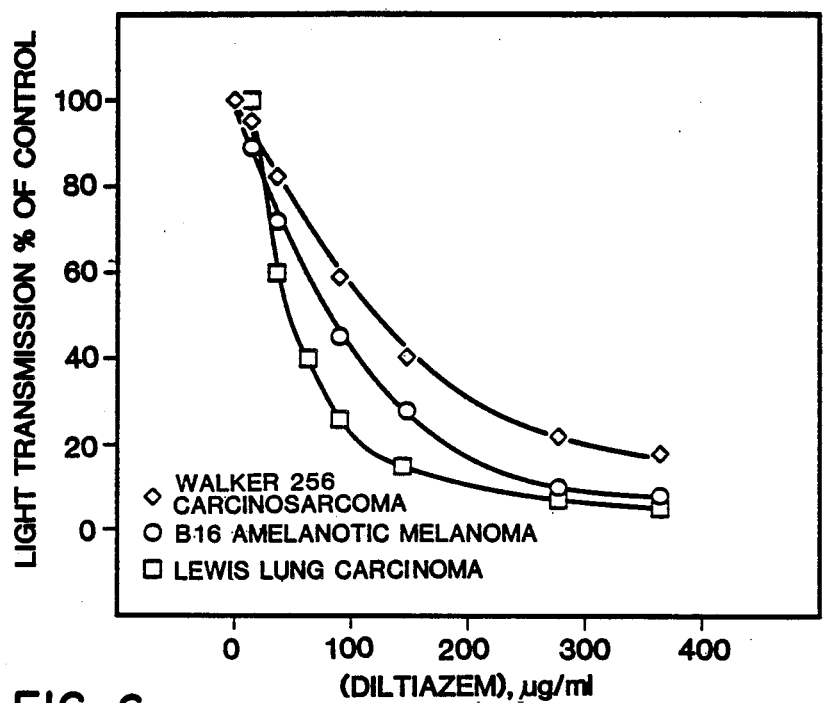
FIG. 6 TUMOR CELL INDUCED PLATELET AGGREGATION
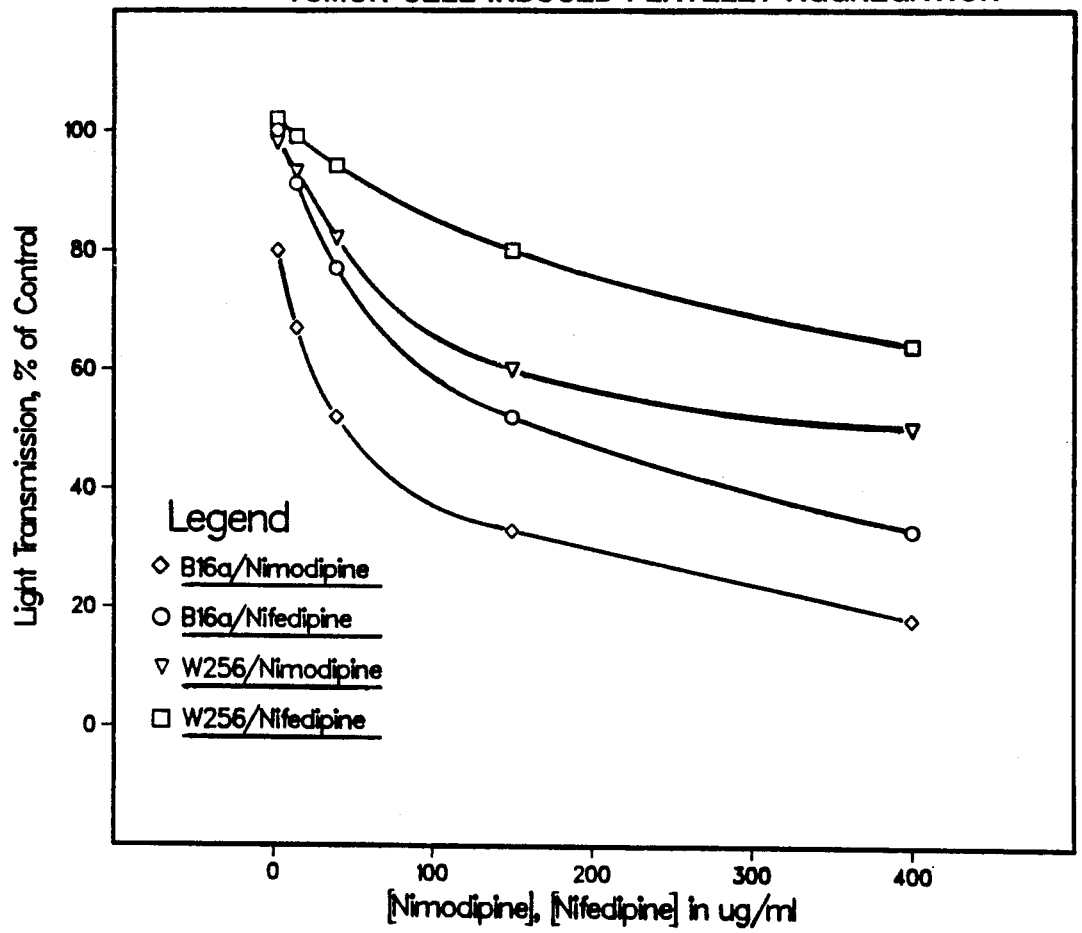

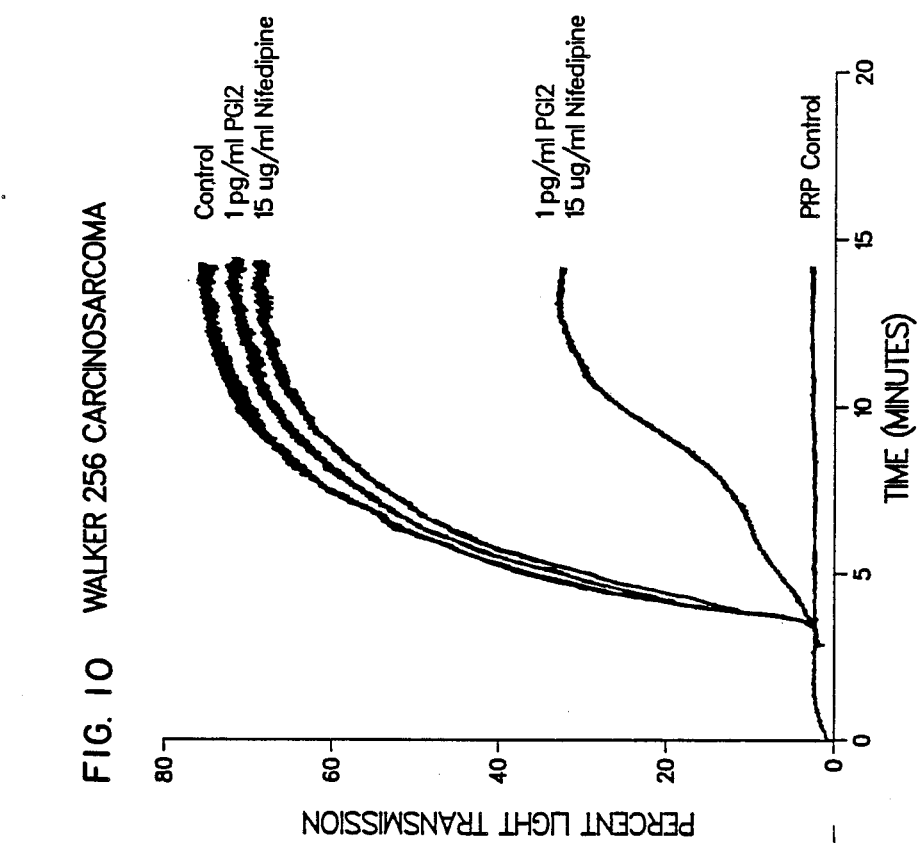
FIG. 10  WALKER 256 CARCINOSARCOMA
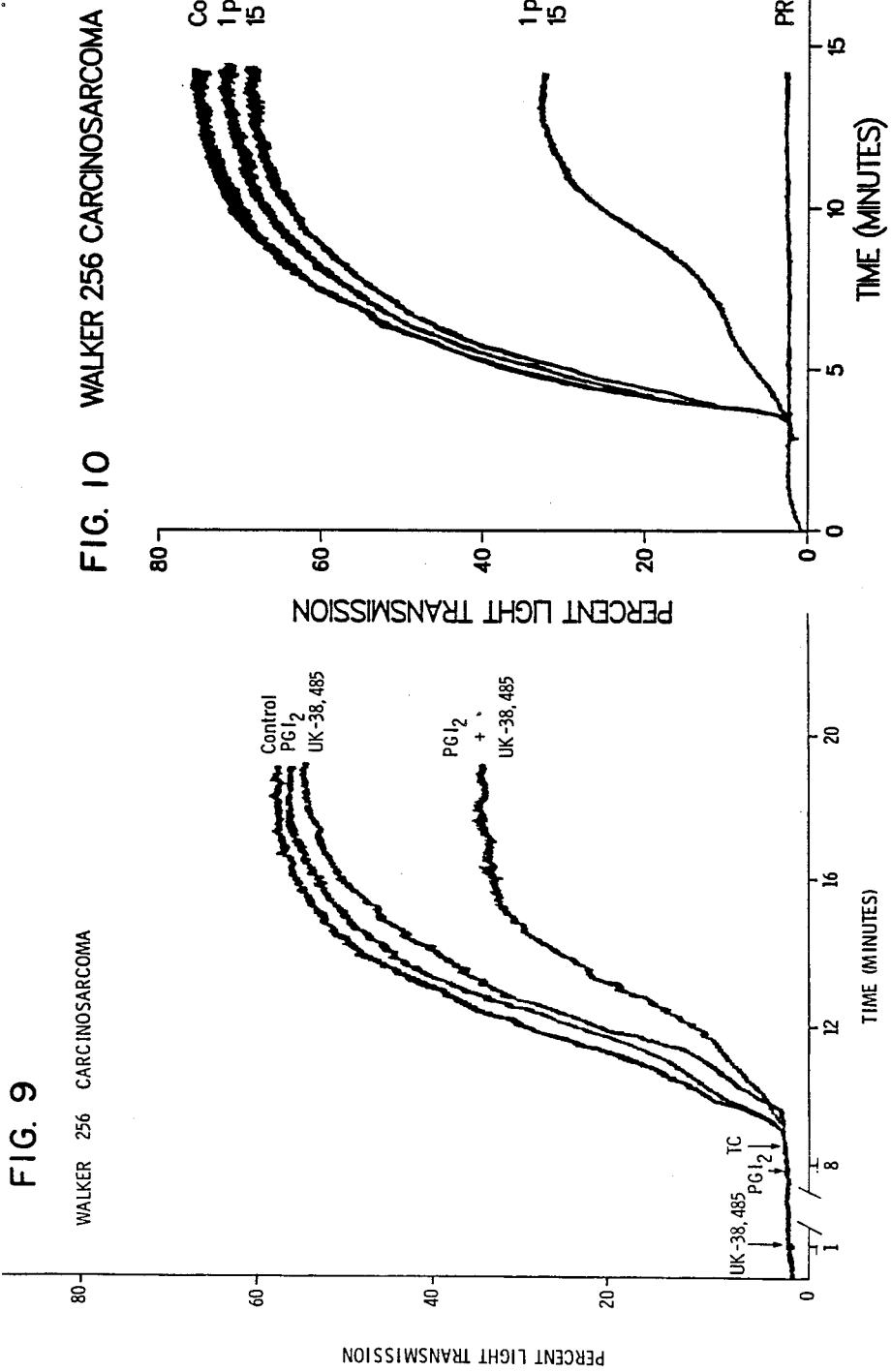
FIG. 9  WALKER 256 CARCINOSARCOMA

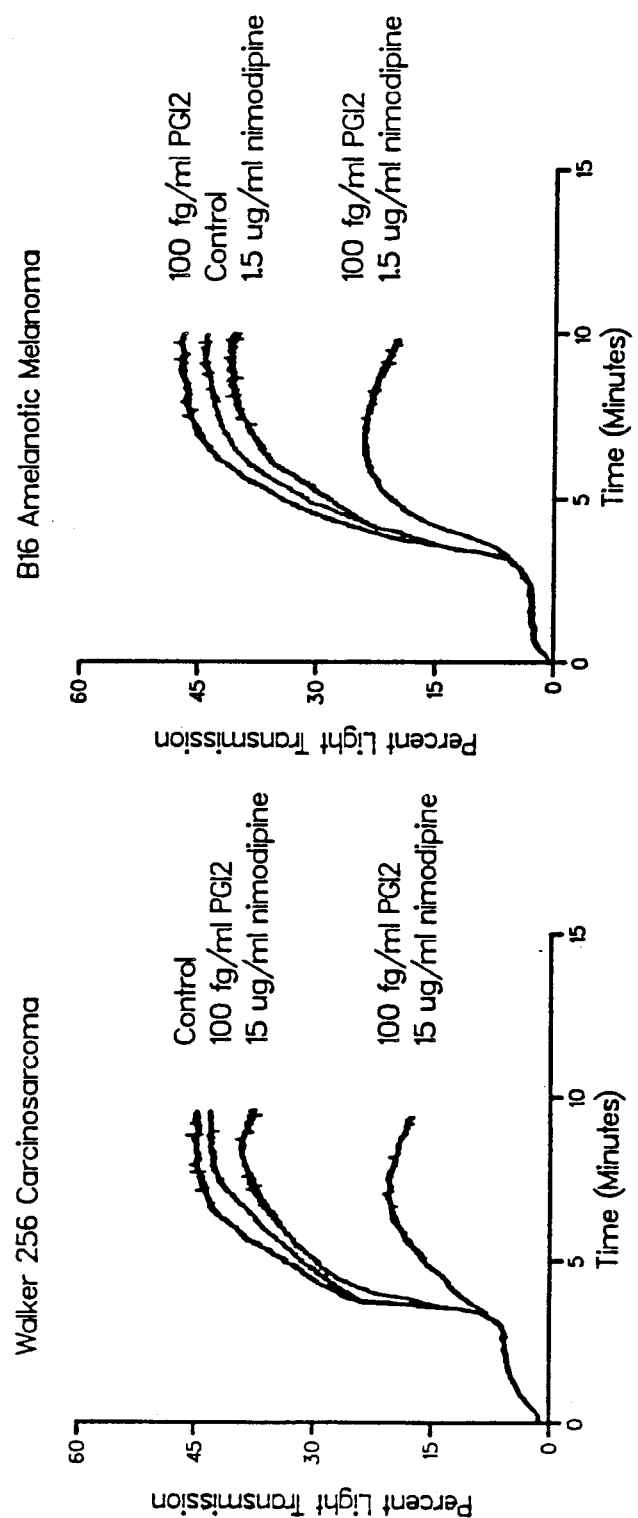

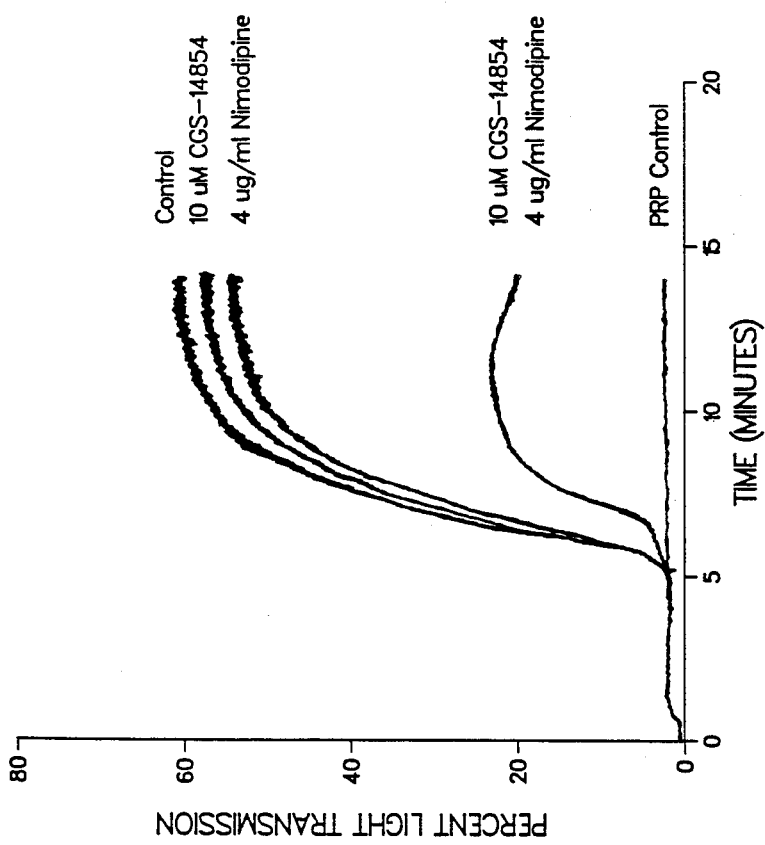
FIG. 13  B16 AMELANOTIC MELANOMA
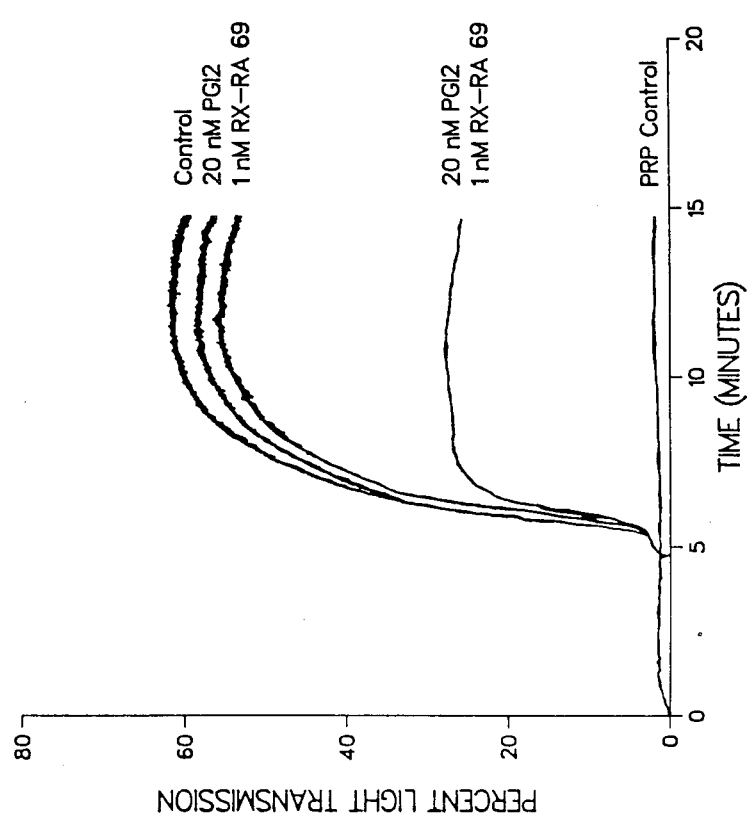
FIG. 12  LEWIS LUNG CARCINOMA

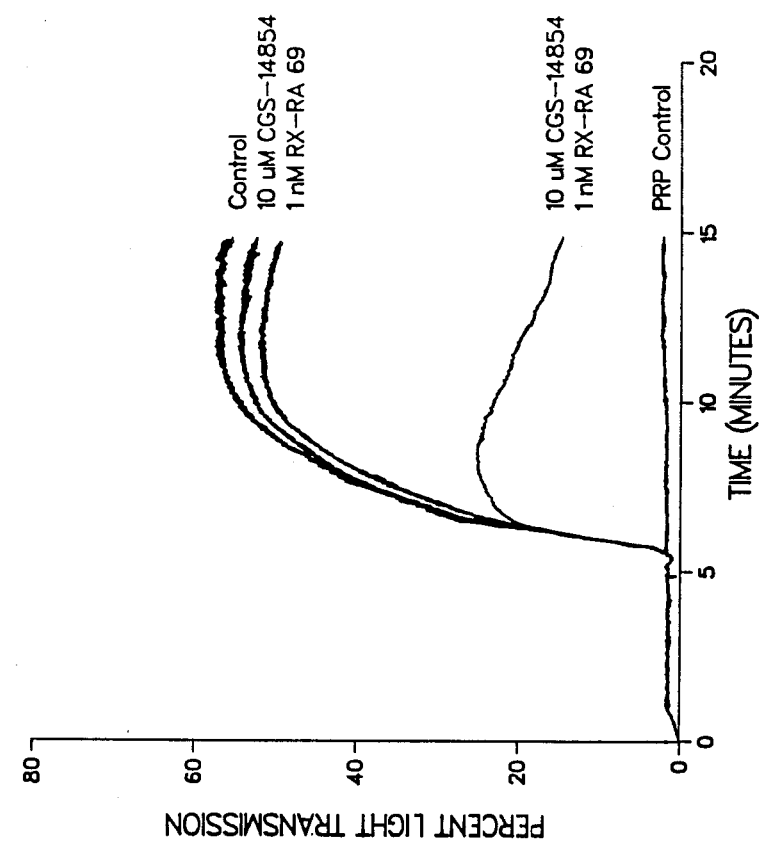
FIG. 15 LEWIS LUNG CARCINOMA
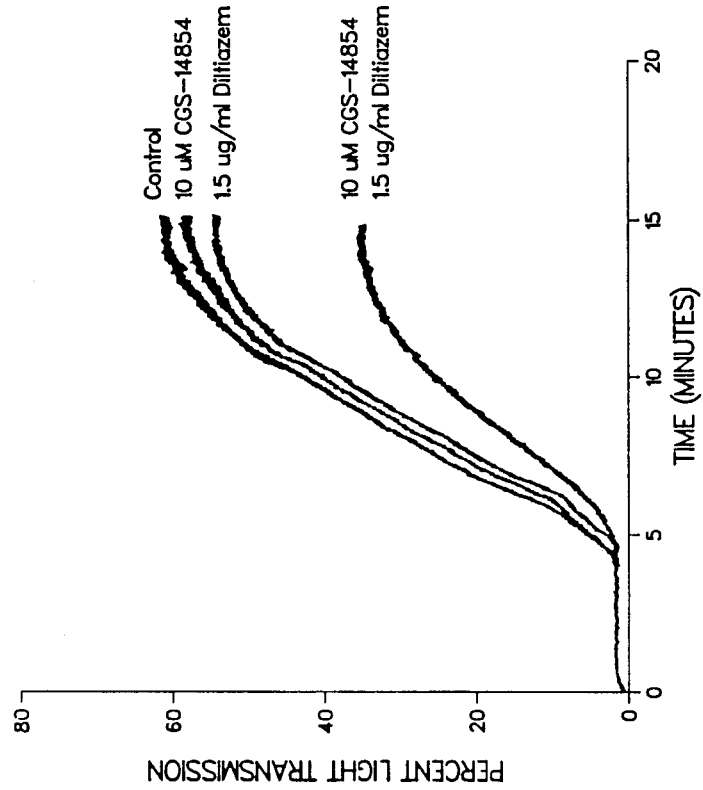
FIG. 14 B16 AMELANOTIC MELANOMA

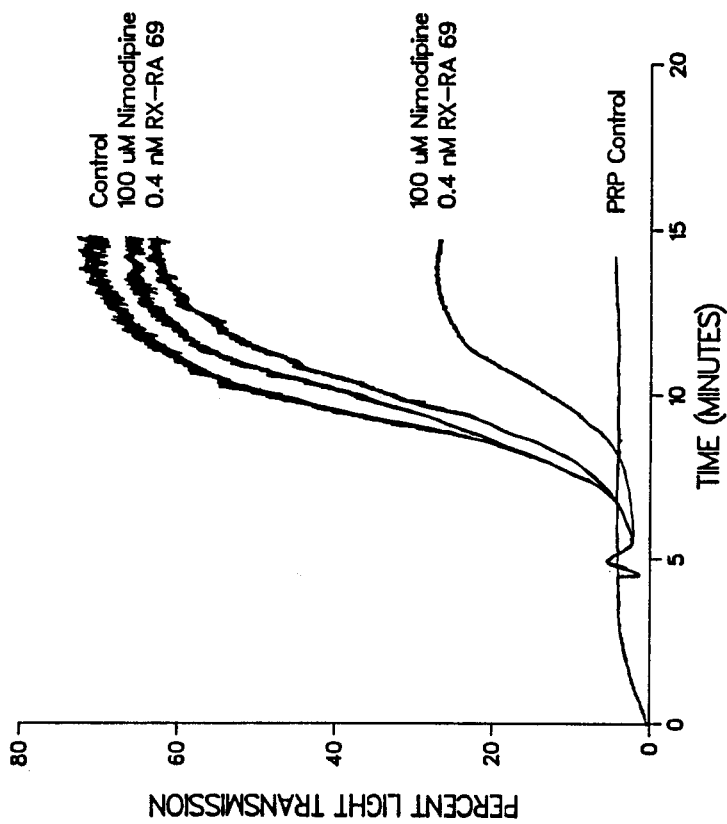
FIG. 17   B16 AMELANOTIC MELANOMA
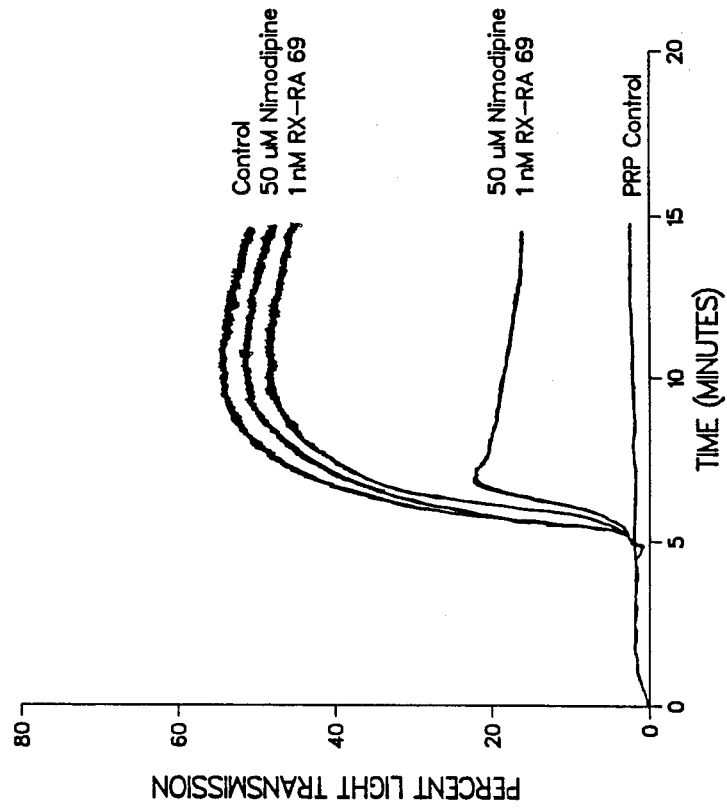
FIG. 16   LEWIS LUNG CARCINOMA

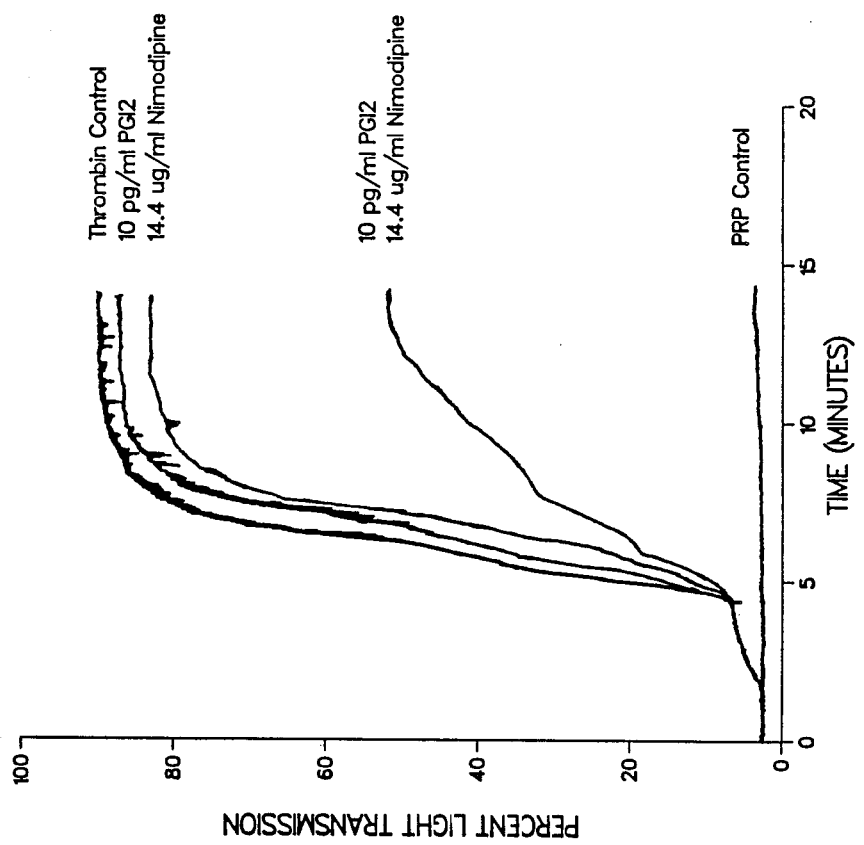
FIG. 19  THROMBIN INDUCED PLATELET AGGREGATION
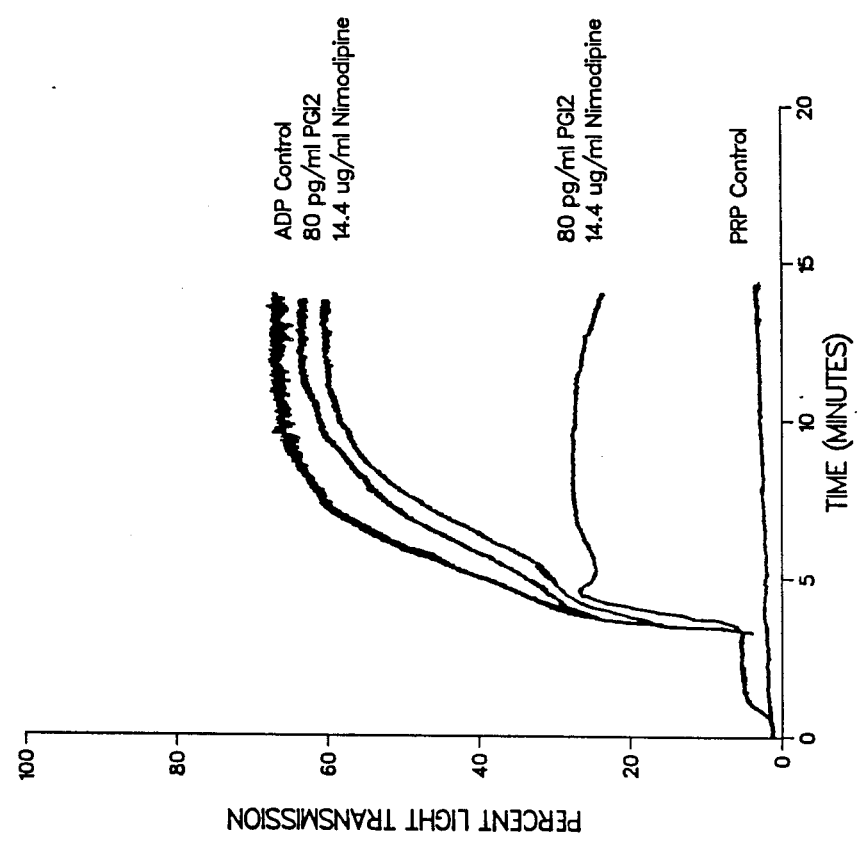
FIG. 18  ADP INDUCED PLATELET AGGREGATION

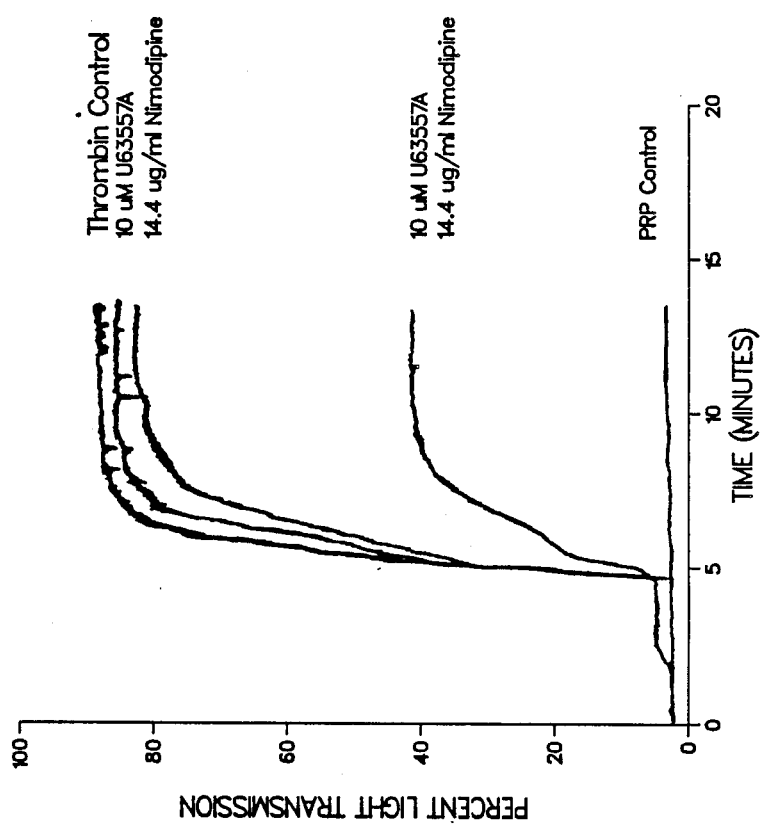
FIG. 21 THROMBIN INDUCED PLATELET AGGREGATION
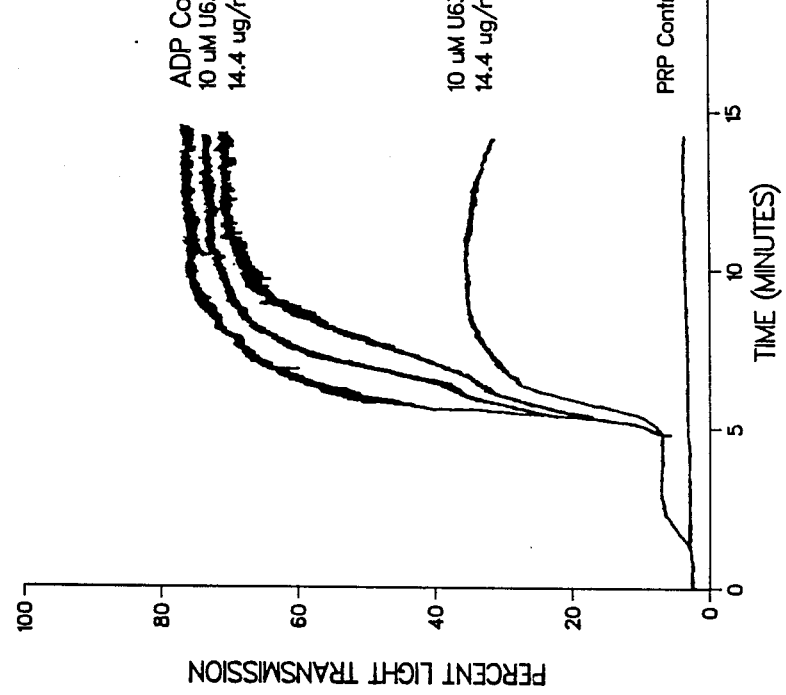
FIG. 20 ADP INDUCED PLATELET AGGREGATION

PLATELET ENHANCED W256 TUMOR CELL ADHESION TO NORMAL RAT ARTERIAL ENDOTHELIUM

A = tumor cells alone
D = tumor cells + platelets + PPP

PLATELET

METHOD AND COMPOSITIONS FOR INHIBITION OF TUMOR CELL INDUCED PLATELET AGGREGATION

CROSS-REFERENCE TO RELATED APPLICATION

This application is a continuation-in-part of U.S. application Ser. No. 480,704, filed Mar. 31, 1983 now U.S. Pat. No. 4,690,935.

BACKGROUND OF THE INVENTION

1. Field of the Invention

The present invention relates to the use for inhibition of tumor cell induced platelet aggregation of admixtures of at least two members of: (1) calcium channel blocker compounds, known for use in the treatment of cardiovascular disorders, such as hypertension, angina and arrhythmia; (2) thromboxane synthase inhibitors, known for use in antithrombotic therapy to inhibit platelet aggregation; (3) phosphodiesterase inhibitors, known for their ability to inhibit platelet aggregation; and (4) prostacyclin (and prostacyclin analogs and stimulating agents), known for their ability to inhibit platelet aggregation. In particular, the present invention preferably relates to the use of admixtures of nimodipine (Bay e 9736), nifedipine (Bay a 1040), diltiazem and all other structurally related and unrelated calcium channel blocking compounds in combination with U63557A, UK 38485, CGS 14854 and all other thromboxane synthase inhibitors; RX-RA 69 and all other phosphodiesterase inhibitors, or prostacyclin, prostacyclin analogs and prostacyclin

2. Prior Art

The primary focus of cancer therapy and research has been directed towards the treatment of the initial or primary tumor. Considerable success has been achieved by utilizing surgery, radiotherapy, and/or chemotherapy. However, it has become increasingly apparent that metastasis, the spread of cancer from the initial tumor to other physically separate sites, is an equally life-threatening situation that must be confronted. The exact steps of metastasis are not known, but it has been demonstrated, that the entrapment or adhesion of circulating tumor cells to endothelial substrata is an important step of the metastatic cascade.

Briefly, the metastatic cascade can be described as a sequence of events that a tumor cell or cells must successfully complete in order to become a metastatic foci. Although different texts vary somewhat in their terminology, the cascade can be thought of as four sequential stages or steps. First, a tumor cell or clump of tumor cells must be "shed" by the primary tumor. Second, the tumor cells must enter the vascular or lymphatic system and avoid destruction by host immune defenses (macrophages, natural killer cells, immune complexes, etc.). Third, the tumor cells must adhere to the endothelial lining or subendothelial lining of the vascular or lymphatic system. Fourth, the adhering tumor cells must avoid dislodgement, extravasate through the endothelium and divide. Tumor cell interactions with host platelets to form a tumor cell-platelet aggregate or thrombus has been shown to be a mechanism that allows tumor cells to successfully complete the last stages of the metastatic cascade.

Platelet aggregation and adhesion are typically thought to be initiated by a number of soluble and non-soluble factors including catecholamines, arachidonic acid metabolites (prostaglandin E2, thromboxane A2), immune complexes, complement components, ADP, and collagen (Gordon, J. L. In: Platelets: Pathophysiology and Antiplatelet Drug Therapy. Alan R. Liss, Inc., New York, pp. 13-17, 1982; Weiss, H. J. In: Platelets: Pathophysiology and Antiplatelet drug Therapy. Alan R. Liss, Inc., New York pp. 13-17, 1982; and Jamieson, G. A., et al. In: Interaction of Platelets and Tumor Cells. Alan R. Liss, Inc., New York, pp. 405-413). Additionally, it has been demonstrated that tumor cells induce platelet aggregation (Gasic, G. J., et al., Int. J. Cancer 11:704-718, 1973; Hara, H., et al., Cancer Res. 40:1217-1222, 1980; and Bastida, E., et al., Nature 291:661-662, 1981). The resultant tumor cell-platelet thrombus can protect the tumor cells from attack by the host immune system, increase the likelihood that the tumor cells would adhere to the endothelial lining or subendothelial lining of the vascular system, and protect adhering tumor cells from dislodgement. Thus, pharmacological agents that inhibit platelet aggregation or reduce platelet number have been investigated for their ability to suppress metastasis (Gasic, G. J., et al., Proc. Natl. Acad. Sci. USA 61:46-52, 1968; Honn, K. V., et al., Science 212:1270-1272, 1981; and Menter, D., et al., In: Prostaglandins and Cancer. First Intl. Conf., pp. 809-813, 1982). Calcium channel blockers are described in U.S. patent application Ser. No. 480,704 (WSU 4.1-2) for this purpose.

Platelet response to aggregating stimuli is a rapid and usually consists of a shape change from the normal discoid shape to a rounding-up, followed by the extrusion of long, thin pseudopodia. Mobilization of $Ca^{++}$ from intracellular stores (probably the dense tubular system) may be the trigger for the shape change and apparently precedes the primary platelet aggregation and the associated dense, alpha, and lysosomal granule release (Shaw, J. O. et al. Biochim. Biophys. Acta 714:492-499, 1982). Although the exact mechanism has not been elucidated, we believe that experimental evidence suggests that an influx of extracellular calcium is required for secondary platelet aggregation (Imai, A., et al., Biochem. Biophys. Res. Commun. 108:(2)752-759, 1982). Both primary and secondary platelet aggregation are associated with phospholipase activation, arachidonic acid metabolism and the formation of cyclooxygenase and lipoxygenase products by stimulated platelets. Phospholipase A2 and C are activated by the increase in intraplatelet $Ca^{++}$ concentration from "resting" levels of $10^{-8}$ to $10^{-7}$ M to activated levels of $10^{-5}$ to $10^{-3}$ M (Gerrard, J. M., et al., In: Platelets in Biology and Pathology—2. J. L. Gordon, ed., North Holland Biomedical Press, Amsterdam, pp. 407-436, 1981). The two phospholipases, however, may be triggered sequentially and not simultaneously by increases in intraplatelet $Ca^{++}$. Phospholipase C may be activated in the primary phase of platelet aggregation by the release of internal stores of $Ca^{++}$ (Rittenhouse-Simmons, S. J. Biol. Chem. 256:(9)4153-4155, 1981; Shukla, S. D. Life Sciences 30:1323-1335, 1982). The activated phospholipase C degrades phosphatidyl inositol which in turn is phosphorylated to phosphatidic acid. Phosphatidic acid may serve as an ionophore to trigger an influx of extra cellular calcium which may activate phospholipase A2 (Serhan, C. N, et al., J. Biol. Chem. 257:(9) 4746-4752, 1982). This activation results in an additional increase phosphatidic acid, the eventual formation of thromboxane A2 (a cyclooxygenase product)

and secondary aggregation (Gorman, R. R. Fed. Proc. 38:(1)83–88, 1979; Parise, L. V., et al., J. Pharm. Expotl. Therap. 222:(1)276–281, 1982). Compounds derived from arachidonic acid (prostacyclin, PGI$_2$ and thromboxane A$_2$, TXA$_2$) have been demonstrated to have a profound but possibly not exclusive (Vargaftig, B. B., et al Biochem Pharmacol. 30 263–271 (1981)) role in platelet aggregation and normal hemostasis. The prior art has demonstrated the formation of TXA$_2$ from the endoperoxide intermediate PGH2 (Hamberg, M., et al., Proc. Natl. Acad. Sci. USA 72:2994, 1975). Subsequently platelet TXA$_2$ biosynthesis was found to be stimulated by numerous aggregating agents and was believed to be an absolute requirement for platelet aggregation (Gorman, R. R., Fed. Proc. 38:83, 1979). This view has recently been challenged by the observations that in some cases the endoperoxide PGH$_2$ can initiate platelet aggregation independent of its conversion to TXA$_2$ (Heptinstall, S., et al., Thromb. Res. 20:219, 1980).

One year following the discovery of TXA$_2$, Vane and co-workers (Moncada, S., et al., Nature 263:663, 1976) discovered PGI$_2$ as a transformation product of prostaglandin endoperoxides. Prostacyclin is produced by vascular tissue of all species so far tested and is the main product of arachidonic acid metabolism in isolated vascular tissue. Prostacyclin is the most potent endogenous inhibitor of platelet aggregation yet discovered, being 30 to 40 times more potent than PGE$_1$ (Moncada, S. et al., In: Biochemical Aspects of Prostaglandins and Thromboxanes, (Eds. N. Kharasch and J. Fried), P. 155. Academic Press, New York, 1977) and 1000 times more potent than adenosine (Mullane, K. M., et al., Eur. J. Pharmacol. 54:217, 1979). In addition, PGI$_2$ can reverse secondary platelet aggregation in vitro (Moncada, S., et al., Prostaglandins. 12:715, 1971) and in the circulatory system of man (Szczeklik, A., et al., J. Pharmacol. Res. Commun. 10:545, 1978). It has been suggested that PGI$_2$ and TXA$_2$ play an antagonistic and pivotal role in the control of thrombosis centered upon their bidirectional (PGI$_2$ increases, TXA$_2$ decreases) effect on platelet cAMP levels.

It has been demonstrated that tumor metastasis is enhanced by tumor cell interactions with platelets and that agents which block or prevent tumor cell-platelet interaction and aggregation have antimetastatic effects (Gastpar, H., J. Medicine 8(2):103–114, 1977; Bastida, E., et al., Cancer Res. 42:4348–4352, 1982; Paschen, W., et al., P. Blut 38:17–24, 1979; Honn, K. V., et al., Acta Clinica Belgica, in press, 1983; and Honn, K. V., et al., Biochem. Pharm., in press, 1983). Agents which have been investigated, function by reducing platelet cell number in the blood or by inhibiting platelet function (aggregation). Recently, calcium channel blockers (verapamil and nifedipine) have been reported to inhibit platelet aggregation induced by epinephrine or ADP (Owen, N. E., et al., Am. J. Physiol. 239:483–488, 1980; Schumunk, G. A. et al., Res. Commun. Chem. Path. and Pharm. 35:(2)179–187, 1982 and Owen, N. E. et al., Am. J. Physiol. 241:613–619, 1981). Because of these recent reports of the inhibitory effects of calcium channel blockers upon platelet aggregation and investigations concerning the interactions between platelet antiaggregatory agents and metastasis, the antimetastatic effects of BAY e 9736 (nimodipine) have been investigated by use in a number of different in vivo and in vitro assay systems as described in U.S. application Ser. No. 480,704. We have demonstrated that the chronic administration of nimodipine to mice will significantly reduce spontaneous metastasis and that prior treatment of nimodipine will reduce metastasis induced by tail vein injection of B16a tumor cells to syngeneic mice. In vitro, we have demonstrated that nimodipine will greatly inhibit platelet aggregation induced by tumor cells and ADP, and increase the reversal rate of aggregated platelets induced by ADP or tumor cells. We have also demonstrated that nimodipine decreases the rate of tumor cell growth over a five day assay period, decreases the rate of incorporation of $^3$H-thymidine into tumor cell DNA, and decreases or inhibits the adhesion of tumor cells to plastic incubation flasks and a virally transformed endothelial cell monolayer.

Our working hypothesis has been that the normal intravascular balance between prostacyclin (PGI$_2$) and platelet arachidonic acid metabolies (i.e., TXA$_2$) can be altered by the presence of a primary tumor and/or circulating tumor cells and their shed (membrane) vesicles. This hypothesis predicts that arachidonic acid metabolism by the tumor cell, platelet and vessel wall is a fundamental determinant in the sum total of their interaction and that PGI$_2$ may be a natural deterrent to metastasis. We have demonstrated that PGI$_2$ is a potent inhibitor of tumor cell induced platelet aggregation (TCIPA) in vitro, and platelet enhanced adhesion of tumor cells to plastic, and endothelial cells (Menter, et al., Cancer Research, 44, 450–456, 1984). We have also demonstrated that PGI$_2$ is a potent antimetastatic agent in vivo and have evidence that endogenous PGI$_2$ production may limit metastasis (Honn K., et al Science 212 1270–1272 (1981). We have also postulated that thromboxane synthase inhibitors could also serve as antimetastatic agents, due to their inhibition of TXA$_2$ induced platelet aggregation in response to tumor cells. In vitro the TX synthase inhibitors of the endoperoxide class inhibit tumor cell induced platelet aggregation (TCIPA) and in vivo inhibit lung colonization from tail vein injected tumor cells. Honn, K., et al J. of Clinical and Exp. Metastasis 1 103–114 (1983). However, imidazole type TX synthase inhibitors do not inhibit TCIPA even in the presence of inhibited TXA$_2$ production. However, these compounds possess antimetastatic activity in vivo in both the tail vein ("experimental metastasis") and spontaneous metastasis models. To explain these apparent discrepancies it is proposed that the in vivo antimetastatic activity of TX synthase inhibitors is due to operation of the "steal hypothesis" which suggests that an inhibition of platelet TXA$_2$ biosynthesis would cause the release of PGH$_2$, the substrate of both prostacylin and thromboxane synthases, which would be absorbed by the vascular endothelium and/or leukocytes. This would cause enhanced PGI$_2$ biosynthesis by the endothelium of the vascular wall and/or by leukocytes.

OBJECTS

It is therefore an object of the present invention to provide synergistic compositions including calcium channel blocker compounds, thromboxane synthase inhibitor compounds, phosphodiesterase inhibitor compounds, and/or prostacyclin, prostacyclin analogs and prostacyclin stimulating agents to inhibit platelet aggregation. These and other objects will become apparent by reference to the following description.

FIGS. 1 to 21 show graphs of tumor cells and platelet interactions as a function of the amount of an agent used to inhibit tumor cell induced platelet aggregation. The greater the reduction in light transmission the greater the reduction in aggregation. As aggregation occurs, the tumor cell-platelet aggregates are clumped together, thereby increasing light transmission.

GENERAL DESCRIPTION

Figure 2:
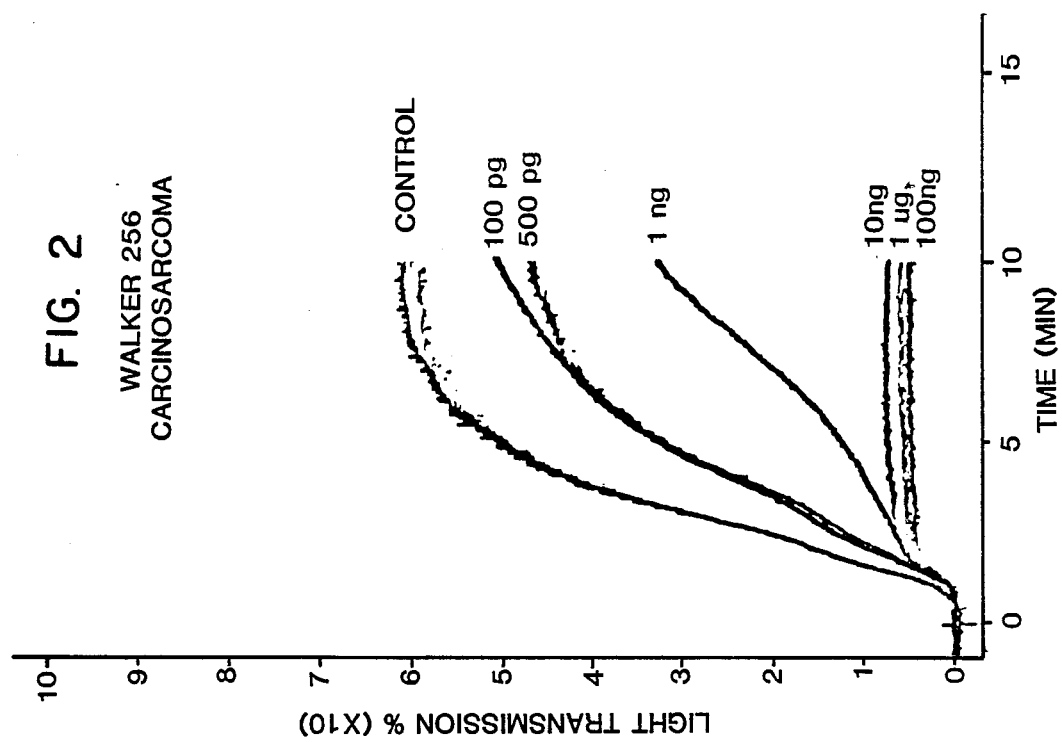
Figure 1:
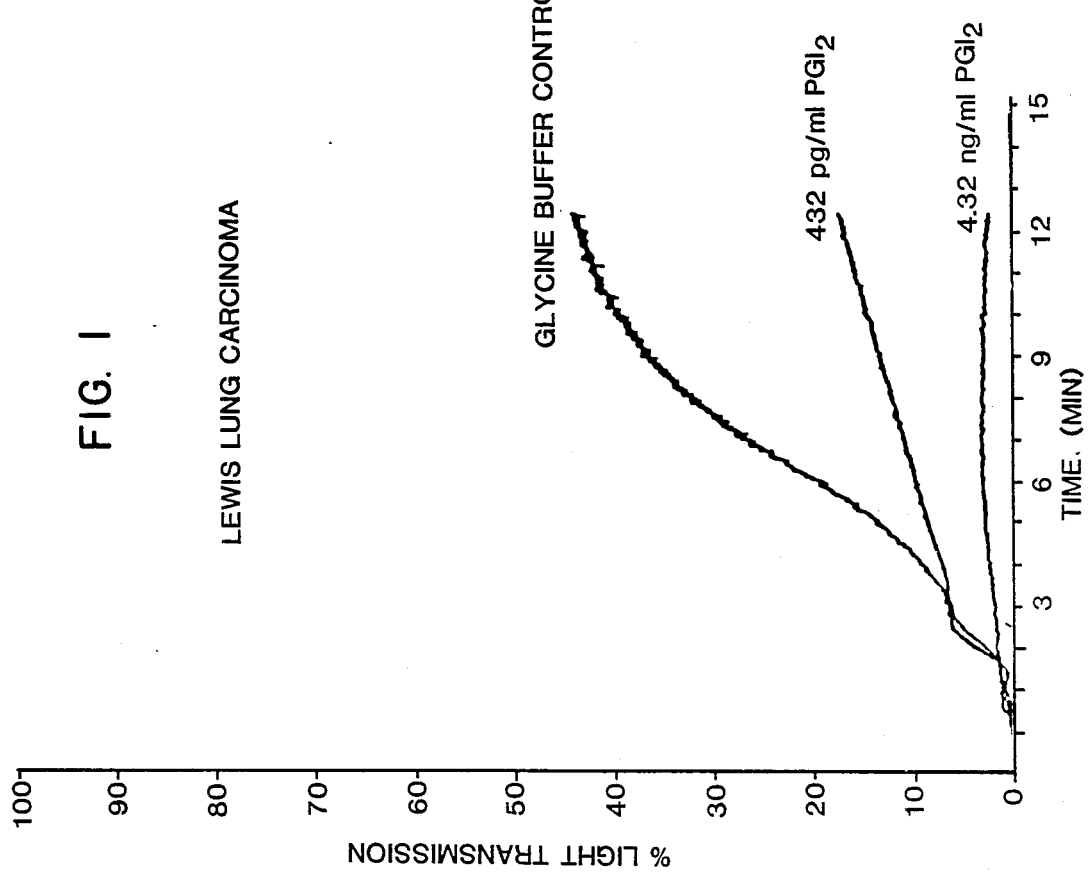
Figure 4:
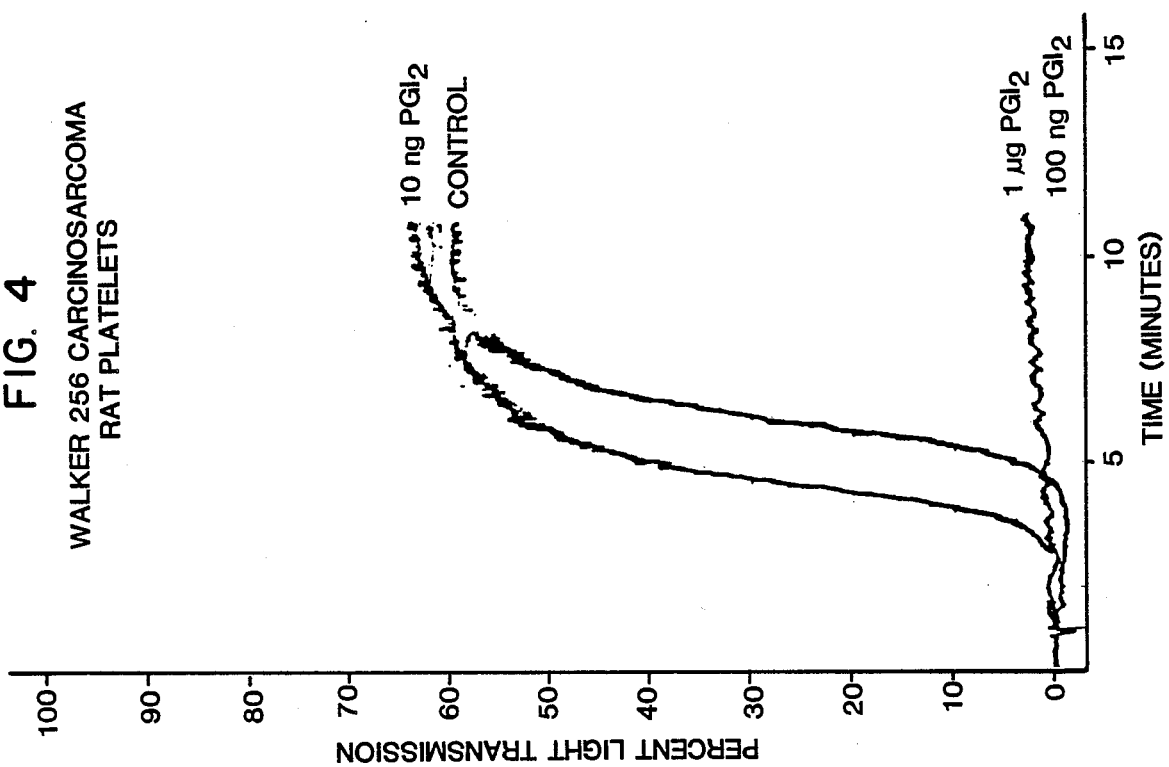
Figure 3:
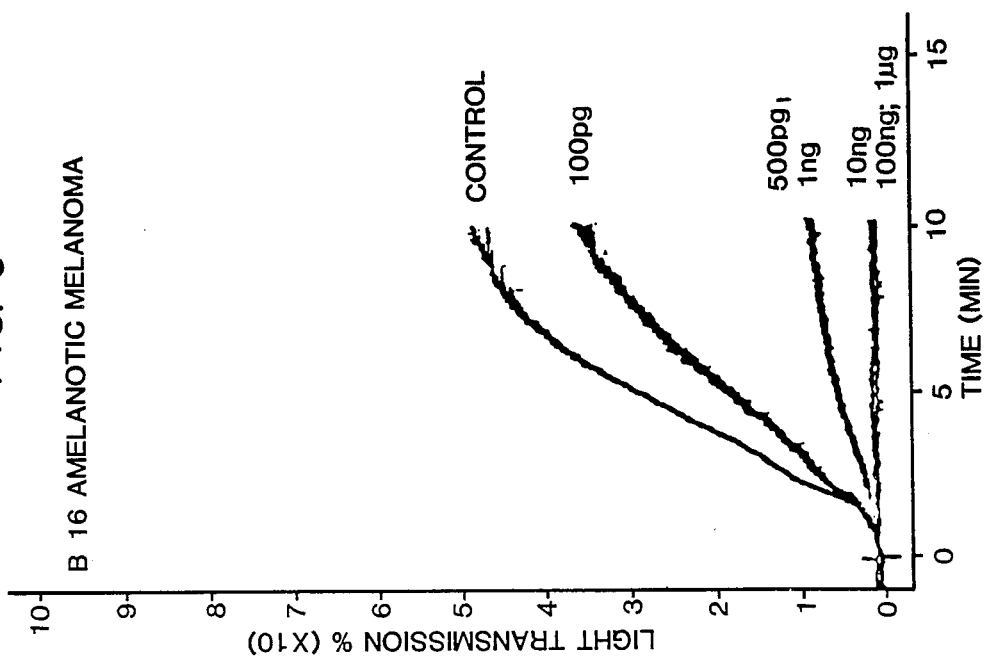

The present invention relates to a composition which inhibits tumor cell induced platelet aggregation comprising an admixture of at least two members of: a calcium channel blocker; a prostacyclin; a thomboxane synthase inhibitor; and a phosphodiesterase inhibitor, wherein each of the members alone inhibit tumor cell induced platelet aggregation in vitro in a first amount and wherein the composition contains a second amount of each member less than the first amount which does not significantly inhibit platelet aggregation alone.

The present invention also relates to a method for inhibiting tumor cell induced platelet aggregation which comprises administering to an animal in need thereof a tumor cell and platelet aggregation inhibiting amount of a composition including at least two members selected from the group consisting of a calcium channel blocker; a prostacyclin a stimulating agent for the prostacyclin; thromboxane synthase inhibitor; and a phosphodiesterase inhibitor.

The organic calcium channel blockers are highly specific and can exert their effects in nanomolar concentrations. The primary work of Fleckenstein A., Am. Rev. Pharmacol. Toxicol. 17:149–166 (1977) determined that these compounds could selectively blockade the calcium channels and electrical functions of muscle tissue.

Four chemical classes of organic calcium channel blockers are currently known: 1. 1,4-dihydropyridine (nimodipine and nefedipine and many others of this class described by the prior art and in Ser. No. 480,704), 2. phenylalkylamine (verapamil), 3. diphenylalkylamine (prenylamine and lidoflazine) and 4. benzothiazepine (diltiazem). In a recent study of receptor binding by CCB, Murphy et al. (Murphy KMM, Gould RJ, Largent BL and Snyder SH. Proc. Natl. Acad. Sci. USA 80:860–864, 1983) demonstrated that the phenylalkylamines, diphenylaklylamines and benzothiazepines all act at a single site on the membrane which is allosterically linked to the dihydropyridine receptor. Diphenylalkylamines and phenylalkylamines decrease the affinity of dihydropyridines for their receptor whereas benzothiazepines increase the affinity. At least one study has shown that phenylalkylamines may act at a site on the inside of the plasma membrane. Calcium channels seem to exist in three distinct states: resting, open and inactivated and the chemical classes of calcium channel blockers differ in their ability to block $Ca^{2+}$ channels in these three states. Phenylalkylamines such as verapamil block $Ca^{2+}$ channels in the open or inactivated state (Nayler WG and Grinwald P. Fed. Proc. Fed. Am. Soc. Exp. Biol.. 40:2855–2861, 1981). Benzothiazepines such as diltiazem bind primarily in the inactivated states (Lee KS and Tsien RW. Nature (London) 302:790–794, 1983). Dihydropyridines such as nitrendipine block $Ca^{2+}$ channels in both their resting and open states. The phenylalkylamine verapamil and the benzothiazepine diltiazem having been described as exhibiting a greater use-dependence than do dihydropyridines, i.e., their $Ca^{2+}$ blocking activity is more dependent upon the frequency of stimulation. Presumably this could be due to differences in binding sites and/or to dihydropyridines binding to $Ca^{2+}$ channels in their resting state rather than in their inactivated state. All of these compounds are well known to those skilled in the art.

MATERIALS AND METHODS In Vitro
Maintenance of B16a Tumors

B16 amelanotic melanoma (B16a), Lewis Lung carcinoma (3LL) and Walker 256 (W256) carcinosarcoma were obtained from the Division of Cancer Treatment, Animal and Human Tumor Bank, Mason Research Institute, Worcester, Mass. Tumors were passaged four times after receipt in syngeneic C57BL/6J male mice (B16a, 3LL) or allogenic Sprague Dawley rats (Walker 256). Passaging involved subcutaneous implantations of tumor pieces (diced to approximately 2×2 mM) into the right auxiliary region using a 18 gauge needle. Mice weighing approximately 20 grams (5 to 7 weeks old) were used to passage the B16a and 3LL cell lines and female rats were used to passage the W256 cell line. Animals were housed under identical conditions of temperature, feeding, photoperiod, etc. The transplanted tumors were allowed to grow for approximately 14 days following implantation.

Platelet Rich Plasma Preparation

Blood (45 ml) was drawn from the antecubital vein of healthy, fasted, aspirin free (for at least two weeks) human volunteers into a plastic syringe containing 5 ml of 4.8% dextrose with 50 U/ml heparin buffered by 25 mM HEPES, pH 7.5. An 18 gauge needle was used to prevent hemolysis. The heparinized blood was gently mixed by inverting the syringe five times and then the blood was transfused into two 40 ml plastic centrifuge tubes and centrifuged for 10 min at 163×g. The resulting platelet rich plasma (PRP; the supernatant fraction) was decanted using an adjustable SMI pipette set at 6 ml. Platelet poor plasma (PPP) was prepared by centrifugation of PRP for 10 min at 1086×g. Platelet poor plasma was to standardize the platelet concentration in PRP to 3±0.2 ×10$^8$/ml. Platelet concentrations were determined using a Coulter Model $Z_{B1}$ cell counter.

Preparation of Rat Platelets

Female rats were anesthetized with sodium pentobarbital (52 mg/kg) and bled via the renal vein. Approximately 9 ml of blood was collected from each rat via an 18 gauge needle into a syringe containing 1 milliliter of 3.8% sodium citrate (for washed rat platelets) or 1 ml of heparin (50 micromoles per ml) for the aggregation studies. Rat platelet-rich plasma (PRP) was prepared in the same manner as the human plasma. The rat PRP was centrifuged at 1500×g×10 min. The supernatant was decanted and saved. The platelet pellet (from citrated PRP) was resuspended in $Ca^{++}/Mg^{++}$-free MEM (Eagle's Minimum Essential Medium Gibco, Grand Island, N.Y.) (with EDTA) to a concentration of 1.2×10$^9$ platelets/ml.

Platelet Wash Solution

10×$Ca^{++}/Mg^{++}$-free Hank's Basic Salt Solution;
80 g NaCl
4 g KCl 0.9 g Na₂HPO₄
0.6 g KH₂PO₄
QS to 1 liter with glass distilled H₂O Stock Wash Solution 100 ml 10×Ca++/Mg++-free Hank's Basic Salt Solution
20 ml 50×MEM Essential Amino Acids
10 ml 100×MEM Non-essential Amino Acids
10 ml 100×MEM Vitamin Solution
10 ml 100×Sodium Pyruvate Solution
1 g Dextrose
10 ml Glutomine at 200 mM
QS to 1 liter with glass distilled water; pH to 7.5 with 4 N NaOH. Filter sterilize with 0.22 M filter; store at 4° C.

Wash Solution #1

50 ml stock wash solution—warm to room temperature. Add 0.8 ml 0.1 M Disodium EDTA (Fisher SO-S-412); pH to 7.5 with 4 N NaOH.

Wash Solution #2

50 ml stock wash solution—warm to room temperature. Bubble O₂ through for 15-20 minutes; pH to 7.5.

Spin platelet-rich plasma for 7 minutes at 1000 G. Aspirate off plasma supernatant with a plastic pasteur pipette. Suspend platelet RBC pellet in Wash Solution #1, using a plastic pasteur pipette. Use the same volume of Wash #1 as original plasma volume. Incubate at room temperature for 15-20 minutes.

Spin Wash #1 platelet-RBC mixture for 7 minutes at 100 G. Aspirate off supernatant with a plastic pasteur pipette. Add Wash Solution #2 to platelet-RBC pellet (use ½ of original plasma volume). Resuspend pellet with a plastic pasteur pipette. Spin platelet-RBC Wash #2 mixture at 160 G for 5-10 minutes. Aspirate off washed platelet suspension supernatant, put into a plastic test tube. Put 10 microliters of the platelet suspension into 20 ml of isoton (Coulter Electronics). Put 4 ml of this platelet-isoton mixture into 20 ml of isoton. Count this final isoton suspension on a Model $Z_{B1}$ Coulter counter using the following settings:

| | |
|---|---|
| Matching Switch | 20 K |
| Gain Trim | 6.5 |
| 1/Amplification | 0.5 |
| 1/Aperture Current | 0.5 |
| Lower Threshold | 6 |
| Upper Threshold | 70 |
| Apperture | 70 M |
| Sample volume | 100 M |

Count the suspension at least four times. Average the counts and correct for coincidence using this equation:

$$\text{True count} = \text{observed count} + \frac{(\text{observed count})^2}{217391}$$

Multiply the true count × 100,000 to obtain platelets/ml. Dilute the platelet suspension (with Wash #2) to obtain a suspension which contains $5.0 \times 10^8$ platelets/ml.

Count the diluted suspension to obtain actual final platelet density. Warm suspension up to 37° C. slowly before using in aggregometer.

(Modification of a procedure in: Mustard et al., Br. J. Haemotology, 1972, 22, 193-204).

Measurement of Platelet Aggregation

Platelet aggregation was measured photometrically using a Sienco Model DP-247E dual channel aggregometer and recorded on a Sienco Model B-5000 dual channel recorder. Aliquots of PRP (250 microliters at $3 \times 10^8$ platelets/ml) were transferred into aggregometry cuvettes and stirred at a constant speed of 800 RPM at 37° C. Platelet studies were designed and run as individually controlled samples. The agent or agents were dissolved in either PEG-400 or glycine buffer (5 mM pH 10.5).

The agent or agents or solvent alone was aliquoted into the cuvettes prior to the addition of the platelet preparations. Immediately after the addition of the platelets, the cuvettes were placed into the aggregometer. After two minutes (to allow for the stabilization of the platelet preparation and mixing of the agent or agents, ADP, thrombin or tumor cells were added in 25.5 or 20 microliter aliquots, respectively, microliter aliquots to induce platelet aggregation. The final concentrations of aggregating stimuli were 10 micromolar ADP, 20 NIH units per ml thrombin and $5 \times 10^5$ tumor cells per ml. The results are shown in FIGS. 1 to 21.

Dispersion and Elutriation of Tumor Cells

Subcutaneous B16a primary tumors were excised, diced and dispersed by collagenase digestion. Tumor pieces (4×4 mm) were divided in approximately 500 mg aliquots and placed in sterile polycarbonate flasks. Ten ml of TDS, "tumor dispersion solution," was added to each flask. TDS was prepared by mixing composition A and Composition B described below.

| Composition A (based on 1 liter) | |
|---|---|
| 9.5 g/l | Sterile Eagles's Minimum Essential Medium (MEM), commercially available from GIBCO, Grand Island, New York |
| 10 ml/l | Non-essential Amino Acids (GIBCO) |
| 10 ml/l | Sodium pyruvate (GIBCO) |
| 0.35 g/l | Sodium bicarbonate (15 mM0) |
| 5.9 g/l | HEPES (25 mM) an organic buffer; commercially available from Sigma Chemical Co., St. Louis, Missouri |
| 150 Units/ml | Penicillin |
| mg/ml | Neomycin sulfate |

The antibiotics were added to ensure that bacterial contamination did not occur.

Composition B is a dry mixture containing collagenase low in clostripain and other proteolytic activity; deoxyribonuclease (DNase) to dissolve deoxyribonucleoprotein released from damaged cell nuclei; lima bean or soybean trypsin inhibitors to exclude any residual tryptic activity; human serum albumin to eliminate nonspecific protease activity and absorb peroxy and hydroperoxy fatty acids liberated from damaged membranes.

| Composition B | Weight/ml Composition A | |
|---|---|---|
| Collagenase (Worthington type III) | 1 | mg/ml |
| DNase I (Sigma Chemical) | 70 | ug/ml |
| Soybean trypsin inhibitor (Worthington) | 100 | ug/ml |
| Human serum albumin (fatty acid-free; | 10 | mg/ml |

| Composition B | Weight/ml Composition A |
| --- | --- |
| Sigma Chemical) | |

Composition B was weighed out and placed in a flask and 100 ml of Composition A added.

The diced tissue in the TDs was then dispersed (15 min., 37° C.) under air in a Dubnoff Metabolic Shaker (90 oscillations/minute). Supernatants were collected through cheesecloth into sterile 50 ml polycarbonate round bottom centrifuge tubes and centrifuged for 10 minutes (25° C.) at 900 rpm (100×g) in a Sorvall SS-34 rotor. Following centrifugation, the supernatant fraction was discarded. The solid cellular matter (pellets) obtained were washed twice with MEM solution, resuspended in MEM and held at 4° C. (a 10 ml portion of TDS added to remaining diced tissue, incubated as above for 45 min, supernatants collected and treated as above.

A 10 ml portion of TDS was added to the remaining diced tissue and the tissue incubated in a metabolic shaker as described hereinabove, except for a period of 60 minutes. The centrifugation was repeated and the resuspended cells were combined.

The cell viability was determined by the vital dye exclusion method (see *Exptl. Cell Res.* 13: 314-347, 1957). The cell count was determined in a hemocytometer. The stromal cell contamination, e.g. macrophage, red blood cells, etc., was determined by visual examination under a microscope. The final cell suspension obtained consisted of greater than 99 percent monodispersed cells with approximately 2 percent host stromal cell contamination. Typical yields from 6 grams of diced tumor cells ranged between 3 to $7 \times 10^8$ dispersed tumor cells.

The final cell suspension were then subjected to centrifugal elutriation for final separation of the tumor cells. In centrifugal elutriation, cells are subject to two opposing forces within a separation chamber; a centrifugal field generated by a spinning rotor and a counterflow of fluid in the opposite (centripetal) direction. A sample suspended in a medium enters the separation chamber. Each cell tends to migrate to a zone where its sedimentation rate is exactly balanced by the flow rate of the fluid through he separation chamber. The chamber's geometry produces a gradient of flow rates from one end to the other; cells with a wide range of different sedimentation rates can be held in suspension. By increasing the flow rate of the elutriating fluid (separation medium) in steps, or by decreasing the rotor speed, successive populations of relatively homogeneous cell sizes can be washed from the chamber. Each population will contain cells which are larger or more dense (i.e., faster sedimenting) than those of previous fractions.

Centrifugal elutriation was accomplished by suspending the tumor cells in a "Tumor Resuspension solution" (TRS), Composition A alone. The suspension was elutriated using a Beckman JE-6 elutriator rotor operating at 1460 rpm in a Beckman J-2-21 centrifuge at 25° C.

A separation medium (Hank's Balanced Salt Solution, MEM or Composition A plus 0.01% albumin (for murine tumor cells) plus 0.1% albumin (for CLA tumor cells)) was pumped through the system using a Cole Palmer Master Flex pump with a NO. 7014 pump head. The pump control box was modified with a 10 turn potentiometer (see *Anal. Biochem.* 98: 112-115, 1979).

The flow rate was measured with a Brooks double-ball flow valve.

Approximately $5 \times 10^8$ to $1 \times 10^9$ cells were injected through an in-line "Y" fitting into the mixing chamber. Cells were loaded into the separation chamber at a flow rate of 6 ml/min. The "Y" position was changed so that only clean Composition A would wash the cells which were then washed at speeds of 6, 9 and 12 ml/min, collecting 100 ml at each flow rate. These were discarded. Cells were collected at 15, 28, 40 and 52 ml/min fractions, 200 ml/fractions. These fractions were recentrifuged ($100 \times g \times 10$ min) and resuspended in 1-2 ml TRS.

Recoveries were generally between 70 to 75 percent of the cells injected into the mixing chamber. Viability determined as previously described. Cell numbers were determined using a Coulter counter (model ZBI; Coulter Electronics).

Preparation of $^{125}$I Radiolabelled Tumor Cells

Walker 256 tumor cells were plated at approximately $5 \times 10^5$ cells/flask. The cells were labelled with $^{125}$I-UDR (iodinated uridine deoxyribonucleic acid) at 0.5 microcuries/ml media (5.0 microcurie/flask). Cells were incubated for approximately 24 hours. The cells from each flask are counted (gamma counter) and have an average count of $0.2 \pm 0.05$ cpm/cell.

In Vitro Attachment Assay

Platelet enhanced tumor cell attachment to endothelial cell monolayers was tested using four conditions: tumor cell alone (Condition A), tumor cells plus washed platelets (Condition B), tumor cells plus platelet poor plasma (Condition C) and tumor cells, washed platelets and platelet poor plasma (Condition D).

Walker 256 tumor cells obtained from culture are radiolabeled with $^{125}$I-UDR as described previously. The radiolabeled cells are removed from T-75 flasks with trypsin (2 milliliters of 0.25% trypsin and 0.01% EDTA) in MEM. After two minutes the flasks are washed 3× with trypsin "quench," 10% fetal calf serum in MEM, to quench and remove the trypsin in order to prevent all cell lysis. The tumor cells were removed from the flasks, centrifuged at $1000 \times g \times 10$ minutes, resuspended in MEM and adjusted to $2.5 \times 10^5$ cells/milliliter. One hundred microliters of the tumor cell suspension ($2.5 \times 10^4$ cells) were plated in 16 mM tissue culture wells (Costar) and overlaid with 250 microliters of Wash Solution #2 (see Platelet Prep). The cells were incubated at room temperature (approximately 22° C.) for 5 minutes. Following this incubation 25 microliters of 7.35 mg/ml $CaCl_2$ were added to the culture wells, 20 microliters of platelet poor plasma (diluted 1:32 with platelet Wash Solution #2) were added to culture wells for conditions C and D and 250 microliters of washed platelets ($3 \times 10^8$/ml final concentration) were added to culture wells for Conditions B and D. Where appropriate, Wash Solution #2 was added to wells (Conditions A and C) so that all wells had the same final volume of solutions. The wells were incubated for one hour at 37° C. After the one hour incubation, the media containing any unattached tumor cells were removed by aspiration and then the wells were washed 2× with 1 ml of sodium phosphate buffer (PBS). To remove the adhering tumor cells from the endothelial cells (from the wells) the trypsin solution is allowed to remain overnight (approximately 16 hrs) instead of 2 minutes. In actuality, the tumor cells are not separated from the endothelial cells; the trypsin dissolves both cell types in the wells. Thus, the aspirated sample which is removed and counter (from each well) contains the remains of the radiolabeled tumor cells as well as the endothelial cells which coated the floor of the well. These tests are indicative of the results in vivo.

Confluent monolayers of normal rat arterial cerebral microvascular endothelial cells were prepared and plated as described in detail in *Laboratory Investigations*, vol. 46, no. 6, p. 534, 1982 (Diglio, C. A., Grammas, P., Giacomelli, F., and Wiener, J.). Briefly, rat endothelial cells were dispersed from corticl microvasculature by collagenase treatment. Migrating cells and cell proliferation are seen. Isolated cells are allowed to proliferate in culture until the expected "cobblestone" appearance characteristic of normal endothelial cells is obtained.

INHIBITION OF TUMOR CELL INDUCED PLATELET AGGREGATION

B16 amelanotic melanoma (B16a), Lewis Lung Carcinoma (3LL) and Walker 256 carcinosarcoma (W256) tumor cells, obtained by the previously described procedure of enzymatic dispersion and centrifugal elutriation were used to test the ability of compounds to inhibit tumor cell induced platelet aggregation.

COMPARATIVE EXAMPLE 1

A 0.212 mg portion of prostacyclin (the sodium salt, Upjohn Co., Kalamazoo, Mich.) was dissolved in 169.6 microliters of glycine buffer (pH 10.1) and serially diluted with the glycine buffer in 10× dilutions. Tumor cell induced platelet aggregation (TCIPA) studies were performed as previously described. The effect of prostacyclin on TCIPA was determined by the addition of 2 microliter aliquots of the serially diluted prostacyclin to heparinized human or rat platelet rich plasma immediately prior to the addition of tumor cells. FIGS. 1 to 4 are representative tracings of the results of a large series of experiments. Prostacyclin, in a dose-dependent manner, inhibits Lewis Lung carcinoma (FIG. 1), Walker 256 carcinosarcoma (FIG. 2) and B16 amelanotic melanoma (FIG. 3) induced aggregation or heparinized human platelets in platelet rich plasma. Additionally, prostacyclin inhibits Walker 256 carcinosarcoma induced aggregation of heparinized rat platelets (platelet rich plasma, FIG. 4). These studies confirm that prostacyclin is a potent inhibitor of platelet aggregation, and were reported by Menter et al (1984). These studies demonstrated the potential use of the aggregometer and tumor cell induced aggregation as a means of screening in vitro for potential antimetastatic agents. Previously, Honn et al (Science 212 1270–1272 1981) had reported that prostacyclin was a potent inhibitor of artificially induced pulmonary metastasis.

COMPARATIVE EXAMPLE 2

Calcium channel blockers have been previously reported to inhibit tumor cell (B16a, 3LL, W256) induced platelet aggregation of heparinized human platelet rich plasma by Honn et al (Clinical and Experimental Metastasis and Hemostatic Mechanisms (1984). Representative examples of calcium channel blocker inhibition of tumor cell induced platelet aggregation are presented in FIGS. 5 and 6. In both figures, all of the calcium channel blockers inhibit TCIPA in a dose-dependent manner. The B16a tumor cell induced platelet aggregation appears to be the most sensitive to inhibition, but all of the tumor cell lines U; tested were inhibited by the calcium channel blockers.

COMPARATIVE EXAMPLE 3

Three structurally different thromboxane synthase inhibiting compounds were tested for ability to inhibit TCIPA. A 3.57 mg sample CGS 14854 (Ciba Geigy, Summit, N.J.) was dissolved in 1 ml of 0.1 N NaOH and the pH was adjusted with 0.2 N HCl to pH 10. Glycine buffer was added to the solution to bring the total volume to 2 ml. CGS 14854 was tested for its ability to inhibit B16a and 3LL tumor cell induced platelet aggregation in heparinized human platelet rich plasma. Five (5) microliter aliquots of serially diluted (0.1 N NaCl in 5 mM glycine buffer, pH 10.5) CGS 14854 were added to the platelet rich plasma 5 minutes prior to the addition of tumor cells. No inhibition of 3LL or B16a induced platelet aggregation was observed at any concentration of CGS 14854 tested, although platelet biosynthesis of thromboxane A2 (as determined by radioimmunoassay of the stable metabolite of thromboxane A2, thromboxane B2) was inhibited in a dose-dependent manner (Table 1). Virtually complete inhibition of platelet biosynthesis of TXA2 was observed at CGS 14854 concentrations of 100 and 100 uM.

TABLE 1

Effect of CGS 14854 on B16 Amelanotic Melanoma (B16a) and Lewis Lung Carcinoma (3LL) Induced Platelet Aggregation.[1]

| | B16a | | 3LL | |
|---|---|---|---|---|
| CGS 14854 | % Control[2] Aggregation | % Control[3] (TXB$_2$) | % Control[4] Aggregation | % Control[5] (TXB$_2$) |
| $10^{-4}$M | 100 ± 0.4 | 9 ± 2.1 | 100 ± 0.9 | 13 ± 0.4 |
| $10^{-5}$M | 98 ± 3.2 | 17 ± 5.7 | 102 ± 2.8 | 23 ± 0.9 |
| $10^{-6}$M | 99 ± 2.1 | 54 ± 3.7 | 104 ± 7.4 | 58 ± 4.5 |
| $10^{-7}$M | 99 ± 0.9 | 77 ± 6.5 | 98 ± 2.9 | 76 ± 6.4 |
| $10^{-8}$M | 101 ± 1.2 | 90 ± 4.8 | 102 ± 3.3 | 95 ± 3.9 |
| $10^{-9}$M | 99 ± 2.3 | 100 ± 5.2 | 101 ± 1.1 | 105 ± 7.6 |

[1] (B16a), (3LL) = 25 ± 2.0 × 10$^6$ cells/ml (platelets) = 3 ± 0.1 × 10$^8$ cells/ml
[2] Control Light Transmittance (Aggregation) = 54 ± 1.1%
[3] Control (TXB$_2$) = 29.4 ± 3.9 n2/ml
[4] Light Transmittance (Aggregation) = 65 ± 3.7%
[5] (TXB$^2$) = 16.9 ± 2.1 n2/ml A 2.83 aliquot of UK 38,485 (Pfizer, Inc. Groton, Conn.) was dissolved in 1 ml of 0.1 N NaOH and the pH adjusted to 10.5 by the addition of 0.2 N HCl. The volume of the solution was increased to 2 ml by the addition of glycine buffer (pH 10.5). The Uk 38,485 solution was serially (10×) diluted with 0.1 N NaCl in 5 mM glycine buffer, pH 10. Five (5) ul aliquots of Uk 38,485 were added to heparinized platelet rich plasma, five minutes prior to the addition of 3LL or W256 tumor cells. No inhibition of 3LL or W256 tumor cell induced platelet aggregation was observed at any concentration of Uk 38,485 tested, although platelet biosynthesis of TXA2 was inhibited in a dose-dependent manner (Table 2). Approximately complete inhibition of TXA2 biosynthesis, as determined by RIA of the stable metabolite of TXA2, TXB2, was observed at Uk 38,485 concentrations 10 and 1 uM.

TABLE 2

Effect of UK 38,485 on Walker 256 Carcinosarcoma (W256) and Lewis Lung Carcinoma (3LL) Induced Platelet Aggregation[1]

| | W256 | | 3LL | |
|---|---|---|---|---|
| UK 38,485 | % Control[2] Aggregation | % Control[3] (TXB$_2$) | % Control[4] Aggregation | % Control[5] (TXB$_2$) |
| $10^{-5}$M | 104 ± 6.8 | 3 ± 0.67 | 98 ± 3.1 | 2 ± 0.7 |
| $10^{-6}$M | 98 ± 2.1 | 24 ± 6.0 | 95 ± 7.9 | 10 ± 3.2 |

TABLE 2-continued

Effect of UK 38,485 on Walker 256 Carcinosarcoma (W256) and Lewis Lung Carcinoma (3LL) Induced Platelet Aggregation[1]

| UK 38,485 | W256 | | 3LL | |
|---|---|---|---|---|
| | % Control[2] Aggregation | % Control[3] (TXB2) | % Control[4] Aggregation | % Control[5] (TXB2) |
| $10^{-7}$M | 101 ± 3.3 | 83 ± 5.8 | 101 ± 2.4 | 87 ± 4.6 |
| $10^{-8}$M | 103 ± 3.8 | 123 ± 25.6 | 97 ± 9.5 | 111 ± 7.1 |
| $10^{-9}$M | 96 ± 5.6 | 108 ± 17.3 | 99 ± 5.7 | 108 ± 16.6 |

[1](B16a), (3LL) = 25 ± 2 × 10^6 cells/ml (platelets), heparinized human = 3 ± 0.2 × 10^8 cells/ml
[2]Control Light Transmittance (Aggregation) = 78 ± 3.1%
[3]Control (TXB2) = 65 ± 13.5 ng/ml
[4]Control Light Transmittance (Aggregation) = 65 ± 2.3%
[5]Control (TXB2) = 38 ± 6.2 ng/ml A 2.75 mg aliquot of U63557A (Upjohn, Kalamazoo, Mich.) was dissolved in 2 ml of 0.9% saline solution. The U63557A solution was serially (10×) diluted with saline, and 5 ul aliquots were added to heparinized human platelet rich plasma 5 minutes prior to the addition of Lewis Lung carcinoma (3LL) tumor cells used to induce platelet aggregation. No inhibition of 3LL tumor cell induced platelet aggregation was observed at any concentration of U63557A tested, although platelet biosynthesis of TXA2 was inhibited in a dose-dependent manner, as determined by RIA of the stable TXA2 metabolite, TXB2 (Table 3). Approximately complete inhibition of platelet biosynthesis of TXA2 was observed at U6557A concentrations of 100 and 10 uM.

TABLE 3

Effect of U63557a on Lewis Lung Carcinoma (3LL) Induced Platelet Aggregation[1]

| | 3LL | |
|---|---|---|
| U63557a | % Control[2] Aggregation | % Control[3] (TXB2) |
| $10^{-4}$M | 41 ± 2.7 | 10 ± 3.1 |
| $10^{-5}$M | 67 ± 1.7 | 18 ± 2.7 |
| $10^{-6}$M | 97 ± 1.5 | 46 ± 4.6 |
| $10^{-7}$M | 101 ± 2.3 | 67 ± 2.6 |
| $10^{-8}$M | 104 ± 5.3 | 94 ± 3.7 |
| $10^{-9}$M | 99 ± 2.1 | 101 ± 2.1 |

[1](3LL) = 25 ± 1 × 10^6 cells/ml (platelets) = 3 ± 0.2 × 10^8 platelets/ml
[2]control Light Transmittance = 53 ± 1.45%
[3]Control (TXB2) = 13.43 ± 1.4 ng/ml

COMPARATIVE EXAMPLE 4

The phosphodiesterase inhibitor RX-RA 69 (Thomae Pharmaceuticals, Federal Republic of Germany) was tested for ability to inhibit B16a and 3LL TCIPA. A 2.12 mg aliquot of RX-RA 69 was dissolved in 1 ml of polyethylene glycol 400 (PEG-400) and serially diluted (1:10 dilutions) with PEG-400. Aliquots of RX-RA 69 (2 to 8 ul) were added to heparinized human platelet rich plasma five minutes prior to the addition of tumor cells. RX-RA 69, in a dose-dependent manner, inhibited B16a and 3LL TCIPA as well as the concomitant platelet biosynthesis of TXA2 (Table 4). Virtually complete inhibition of platelet aggregation was observed with RX-RA 69 concentrations of 1.0 uM and higher.

TABLE 4

Effect of RX-RA 69 on B16 Anclanator Melanoma (B16a) and Lewis Lung Carcinoma (3LL) Induced Platelet Aggregation[1]

| RX-RA 69 | % Control[2] Aggregation | % Control[3] (TXB2) | % Control[4] Aggregation | % Control[5] (TXB2) |
|---|---|---|---|---|
| $10^{-5}$M | 5 ± 0.2 | 11 ± 0.58 | 2 ± 0.1 | 16 ± 10.1 |
| $10^{-6}$M | 5 ± 0.6 | 16 ± 0.77 | 7 ± 0.2 | 18 ± 5.1 |
| $10^{-7}$M | 24 ± 0.8 | 43 ± 4.2 | 18 ± 2.1 | 16 ± 1.5 |

TABLE 4-continued

Effect of RX-RA 69 on B16 Anclanator Melanoma (B16a) and Lewis Lung Carcinoma (3LL) Induced Platelet Aggregation[1]

| RX-RA 69 | % Control[2] Aggregation | % Control[3] (TXB2) | % Control[4] Aggregation | % Control[5] (TXB2) |
|---|---|---|---|---|
| $10^{-8}$M | 51 ± 2.9 | 52 ± 7.2 | 27 ± 3.3 | 43 ± 12.2 |
| $10^{-9}$M | 86 ± 2.6 | 88 ± 8.5 | 66 ± 3.1 | 86 ± 1.11 |
| $10^{-10}$M | 98 ± 3.9 | 109 ± 13.0 | 102 ± 2.7 | 104 ± 9.3 |

[1](W256), (3LL) = 25 ± 2 × 10^6 cells/ml (platelets) = 3 ± 1 × 10^8 cells/ml
[2]Control Light Transmittance = 85 ± 2.1%
[3]Control (TXB2) = 3.8 ± 2.6 ng/ml
[4]Control Light Transmittance = 51 ± 3.9%
[5]Control (TXB2) = 14.7 ± 2.81 ng/ml

SYNERGISTIC (MULTI-DRUG) INHIBITION OF PLATELET AGGREGATION

Compounds described in Comparative Examples 1 to 4, which inhibit platelet aggregation and/or platelet biosynthesis of TXA2, were examined for ability to additively or synergistically inhibit platelet aggregation induced by elutriated B16a, 3LL, or W256 tumor cells. Briefly, pairs of the previously described compounds were tested in combination at concentrations which by themselves had little (approximately 10%) or no inhibitory effect on platelet aggregation. As described below, however, the precise combination of drugs could cause significant inhibition of platelet aggregation and platelet biosynthesis of TXA2. In all of the following examples (5–12), the drugs tested were prepared as previously described, and the specific concentration of a drug used to test for additive/synergistic inhibitory effects, was determined by testing varying concentrations of the drug in order to obtain a concentration which had little or no inhibitory effect on platelet aggregation. If a drug concentration was utilized which, by itself, inhibited TCIPA by more than 10 to 20%, then little or no additive/synergistic inhibitory effects were observed when that drug was tested in combination with another compound, regardless of the concentration of the second compound.

EXAMPLE 5

Figure 8:
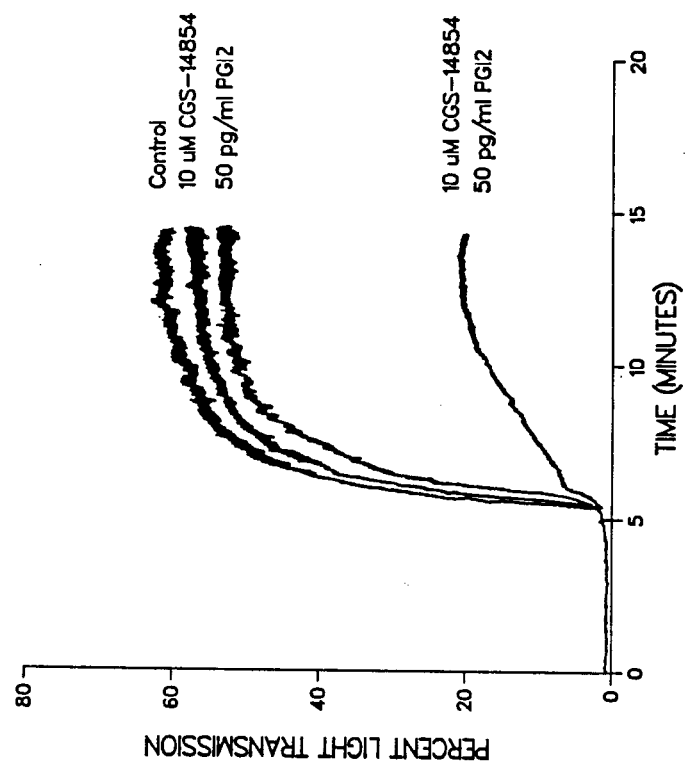
Figure 7:
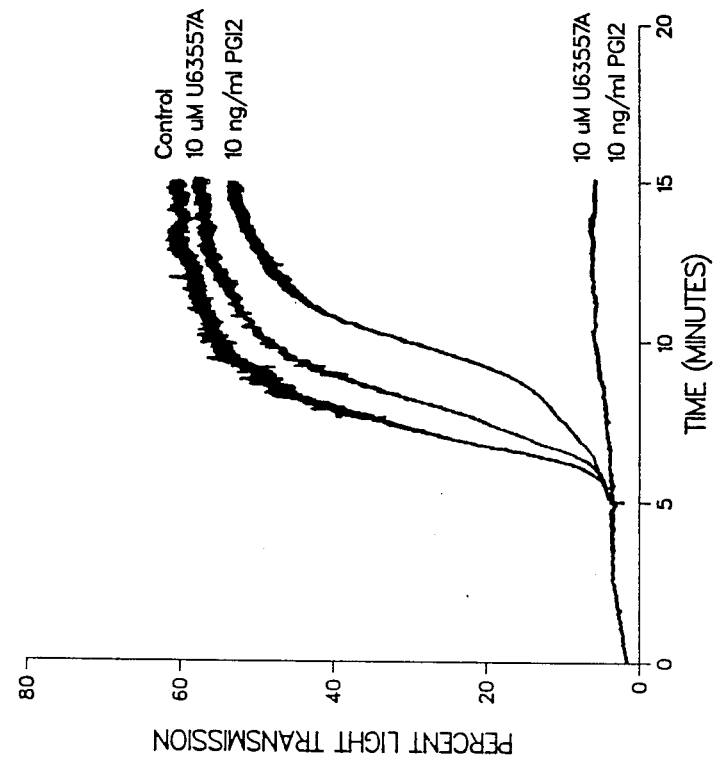

The prostaglandin PGI2 (prostacyclin) in combination with the thromboxane synthase inhibitor U63557A, CGS 14854, or UK 38,485 can synergistically inhibit 3LL or W256 induced platelet aggregation (in heparinized human platelet rich plasma). FIG. 7 depicts the synergistic effects of 10 ng/ml PGI2 (26.7 nM PGI2) and 10 uM U63557a inhibiting 3LL TCIPA. FIG. 8 depicts the synergistic effects of 50 pg/ml PGI2 (133 pM PGI2) and 10 uM CGS 14854 inhibiting 3LL TCIPA. (These assays utilized different blood donors and different 3LL preparations which most probably accounts for the varying concentrations of PGI2 necessary to demonstrate synergistic inhibition of 3LL TCIPA.) FIG. 9 depicts the synergistic effects of 100 fg/ml PGI2 (267 fM PGI2) and 10 uM UK 38,485 inhibiting W256 TCIPA.

EXAMPLE 6

The prostaglandin PGI2 (prostacyclin) in combination with the calcium channel blocker nimodipine (Bay e 9736) or nifedipine (Bay a 1040) synergistically inhibits W256 or B16a TCIPA in heparinized human platelet rich plasma. FIG. 10 depicts the synergistic effects of 1 pg/ml PGI2 (2.67 Pm PGI2) and 15 ug/ml nifedipine (43.3 uM Nifedipine) inhibiting W256 TCIPA. FIG. 11a depicts the synergistic effects of 100 fg/ml PGI2 (267 fM PGI2) and 15 ug/ml nimodipine (35.8 uM nimodipine) inhibiting W256 TCIPA. FIG. 11b depicts the synergistic effects of 100 fg/ml PGI2) and 1.5 ug/ml nimodipine (3.6 uM nimodipine) inhibiting B16a TCIPA. In FIGS. 10 and 11a, 11b, the concentration of PGI2 and the nimodipine are not constant. These differences are due to different blood donors (differing platelet sensitivity to inhibition by PGI2, etc.) and to differences in ability (potency) of B16a and W256 tumor cell lines to induce platelet aggregation.

EXAMPLE 7

The prostaglandin PGI2 (prostacyclin) in combination with the phosphodiesterase inhibitor RX-RA 69 can synergistically inhibit 3LL TCIPA in heparinized human platelet rich plasma. FIG. 12 depicts the effects of 20 nM PGI2 and 1 nM RX-RA 69. Either drug, along, has little inhibitory effect on 3LL TCIPA. In combination, however, the drugs significantly inhibit 3LL TCIPA.

EXAMPLE 8

The thromboxane synthase inhibitor CGS 14854 in combination with the calcium channel blocker nimodipine (Bay e 9736) or the phosphodiesterase inhibitor RX-RA 69 synergistically inhibits B16a or 3LL TCIPA in heparinized human platelet rich plasma. FIG. 13 depicts the synergistic effects of 10 uM CGS 14854 and 4 ug/ml nimodipine (9.6 uM nimodipine) inhibiting B16a TCIPA. FIG. 14 depicts the synergistic effects of 10 uM CGS 14854 and 1.5 ug/ml diltiazem (3.6 uM diltiazem) inhibiting B16a TCIPA. FIG. 15 depicts the synergistic effects of 10 uM CGS 14854 and 1 nM RX-RA 69 inhibiting 3LL TCIPA. In the three experiments represented by FIGS. 13 to 15, the drugs alone had little or no inhibitory effects on TCIPA, but in combination function to significantly (and synergistically) inhibit TCIPA.

EXAMPLE 9

The calcium channel blocker nimodipine (Bay e 9736) in combination with the phosphodiesterase inhibitor RX-RA 69 synergistically inhibits 3LL and B16a TCIPA in heparinized human platelet rich plasma. FIG. 16 depicts the synergistic effects of 50 uM nimodipine and 1 nM RX-RA 69 inhibiting 3LL TCIPA. FIG. 17 depicts the synergistic effects of 100 uM nimodipine and 0.4 nM RX-RA 69 inhibiting B16a TCIPA. The concentration of nimodipine and RX-RA 69 utilized in the FIGS. 16 and 17 are different because of minor differences in donor platelet sensitivity to the drugs as well as to the differences between 3LL and B16a in ability (strength of stimulus) to induce platelet aggregation.

EXAMPLE 10

The calcium channel blocker nimodipine (Bay e 9736) in combination with the prostaglandin PGI2 (prostacyclin) synergistically inhibits both ADP and thrombin induced platelet aggregation in heparinized human platelet rich plasma. FIG. 18 depicts the synergistic effects of 80 pg/ml (213.6 pM PGI2) and 14.4 ug/ml nimodipine (34.4 uM nimodipine) inhibiting ADP (10 uM) induced platelet aggregation. FIG. 19 depicts the synergistic effects of 10 pg/ml PGI2 (26.7 pM PGI2) and 14.4 ug/ml nimodipine (34.4 uM nimodipine) inhibiting thrombin (20 NIH units/ml) induced platelet aggregation. Differences in concentrations of PGI2 used in the experiments represented by FIGS. 18 and 19 reflect donor platelet differences in sensitivity to the antiaggregatory actions of PGI2.

EXAMPLE 11

The calcium channel blocker nimodipine (Bay e 9736) in combination with the thromboxane synthase inhibitor U63557A synergistically inhibit both ADP and thrombin induced platelet aggregation in heparinized human platelet rich plasma. FIG. 20 depicts the synergistic effects of 14.4 ug/ml nimodipine (34.4 uM nimodipine) and 10 uM U63557A inhibiting ADP (10 uM) induced platelet aggregation. FIG. 21 depicts the synergistic effects of 14.4 ug/ml nimodipine (34.4 uM nimodipine) and 10 uM U63557A inhibiting thrombine (20 NIH units/ml) induced platelet aggregation.

SYNERGISTIC (MULTIDRUG) INHIBITION OF TUMOR CELL ADHESION

Walker 256 carcinosarcoma (W256) tumor cells, obtained by the previously described procedure for the radiolabeling of cultured W256 cells were used to test the ability of a calcium channel blocker and a thromboxane synthase inhibitor compound to inhibit tumor cell adhesion to a confluent monolayer of rat endothelial cells. Drugs were prepared in a manner similar to that previously described.

EXAMPLE 12

Figure 22:
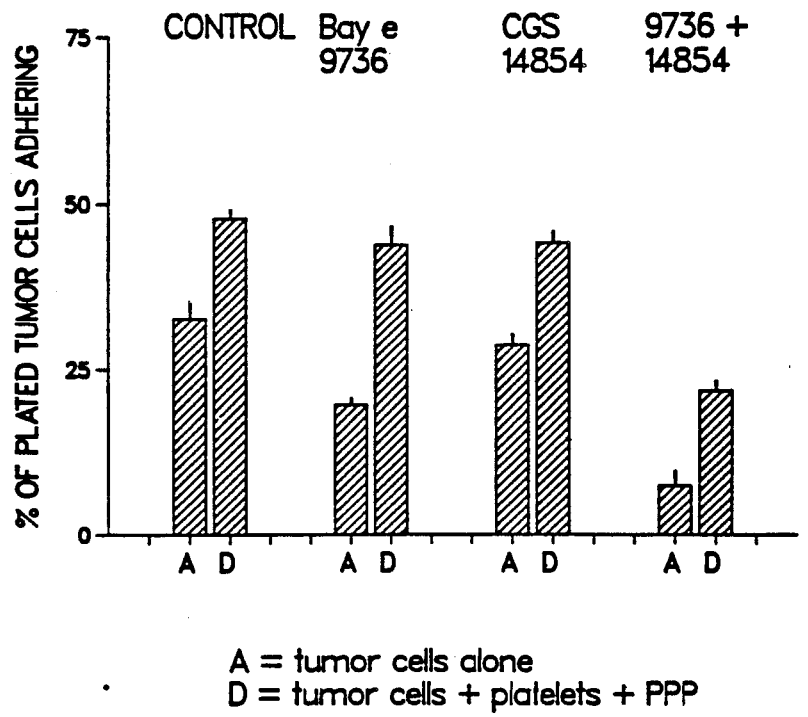
FIG. 22 is a graph showing tumor cell adhesion to rat arterial endothelium as a function of the use of compounds which inhibit tumor cell induced platelet aggregation.

The effect of the calcium channel blocker nimodipine on Walker 256 tumor cell adhesion to plastic wells or to confluent monolayers of virally transformed endothelial cells has been previously disclosed in U.S. application Ser. No. 480,704 (4.1-2). The effect of a combination of the calcium channel blocker nimodipine (50 uM) and the thromboxane synthase inhibitor CGS 14854 (10 uM), which by themselves, have no effect of W256 tumor cell adhesion to confluent monolayers of normal rat arterial endothelial cells was examined. In combination, the two compounds synergistically inhibited tumor cell adhesion as shown in FIG. 22. Similar results can be achieved with other combinations based upon previous experience with this test method.

SYNERGISTIC EFFECT OF VARIOUS CALCIUM ACTIVE COMPOUNDS ON PLATELET AGGREGATION

Figure 23:
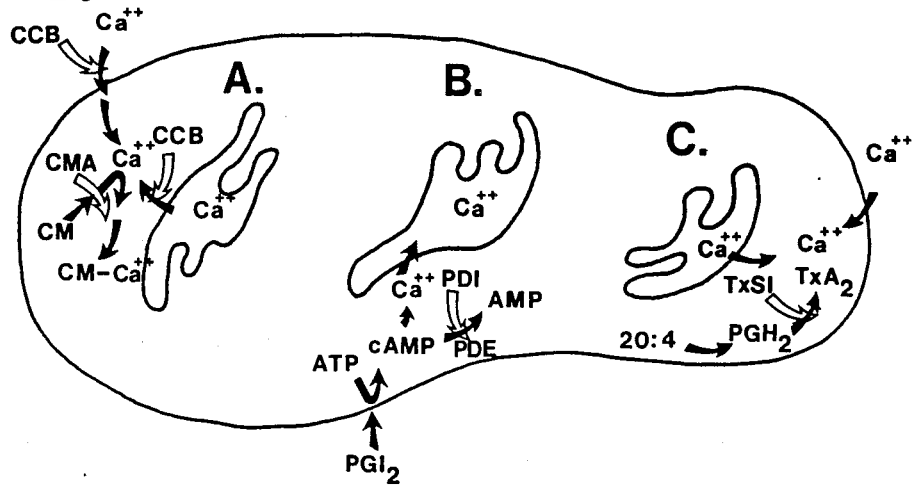
FIG. 23 is a schematic view of a platelet showing the interaction of the compounds described in the application on platelet calcium ion levels.

FIG. 23 shows the affect of various calcium active compounds on the platelet. The definitions are:

LEGEND

CCB = Calcium Channel Blockers
TXSI = Thromboxane Synthase Inhibitors
20:4 = Arachidonic Acid
CM = Calmodulin
CHP = Dihydropyridine
$Ca^{++}$ = Calcium
CMA = Calmodulin Antagonist
$PGI_2$ = Prostacyclin
ATP = Adenosine Triphosphate
cAMP = Cyclic AMP
AMP = Adenosine Monophosphate
PDE = Phosphodiesterase
PDI = Phosphodiesterase Inhibitor
$PGH_2$ = Prostaglandin Endoperoxide $H_2$
$TXA_2$ = Thromboxane $A_2$ The ultimate biochemical messenger in platelet aggregation is the release of sequestered stores of intraplatelet calcium and the influx of extracellular calcium. Considerable debate centers on the temporal relationship between these two events, however, there is agreement that both intracellular and extracellular calcium are required for platelet aggregation whether in response to tumor cells or normal agonists such as thrombin. We have shown that since a variety of platelet inhibitory agents act either directly or indirectly to inhibit calcium mobilization and/or enhance sequestration of calcium that these agents function in a synergistic manner when put in combination. The agents listed in the above FIG. 23 are calcium channel blockers, calmodulin antagonists, prostacyclin, phosphodiesterase inhibitors and thromboxane synthase inhibitors. The action of calcium channel blockers and calmodulin antagonist is depicted in part A. Calcium channel blockers of the dihydropyridine, phenylalkylamine and benzothiazepine classes have been shown to inhibit platelet aggregation induced by ADP, thrombin and tumor cells. The exact site of action is currently unknown. Calcium channel blockers may prevent the entry of extracellular calcium as depicted in FIG. 23. Alternatively, they may prevent the release of calcium from intracellular stores. Finally, calcium channel blockers may function as calmodulin antagonists. In addition, to calcium channel blockers there are an emerging group of compounds (i.e., trifluoperazine and calmidazolium) which oppose the action of calmodulin. Calmodulin is an ubiquitously distributed protein which contains four binding sites for calcium and 16 theoretically confirmational states. Interaction of calcium with calmodulin can cause both positive and negative effects on subsequent events such as phosphorylation of key intracellular and/or intraplatelet proteins. In B depicted in FIG. 23 we see the relationship between prostacyclin, cyclic AMP and phosphodiesterase inhibitors. Prostacyclin interacts with the specific receptors on the platelet plasma membrane to cause a conversion of ATP to cyclic AMP. Cyclic AMP is a multi-faceted intracellular second messenger. Prostacyclin through the action of cyclic AMP causes the sequestration of intracellular calcium from the free state to the bound state. Phosphodiesterase is an enzyme which causes the hydrolysis of cyclic AMP to its inactive metabolite AMP. Phosphodiesterase inhibitors by inhibiting the enzyme phosphodieserase prolong the biological half-life of cyclic AMP and potentiate the action of prostacyclin or any other agent which stimulates cyclic AMP. The generation of thromboxane $A_2$ is depicted in C. Thromboxane $A_2$ is the ultimate biological mediator of arachidonic acid metabolism in the platelet. Thromboxane $A_2$ has been reported to both stimulate the release of intraplatelet calcium and ehnace the influx of extraplatelet calcium. Thromboxane synthase inhibitors, by blocking the enzyme thromboxane synthase, prevent the formation of thromboxane $A_2$. We have shown that any of the above mentioned compounds can be combined to produce a synergistic response on intraplatelet calcium mobilization and/or $Ca^{2+}$ influx and hence prevention of platelet aggregation. We have specifically combined calcium channel blocker compounds with phosphodiesterase inhibitors, prostacyclin with calcium channel blocker compounds, prostacyclin with thromboxane synthase inhibitors and calcium channel blocker compounds with thromboxane synthase inhibitors.

Based upon Applicants' experience with the calcium channel blocker compounds as described in Ser. No. 480,704, the inhibition of tumor cell induced platelet aggregation in vitro has been shown to be predictive of antimetastatic activity in vivo. The use of the combinations of the claimed agents in vivo is expected to significantly inhibit tumor cell induced metastasis.

We claim:

1. A composition which inhibits tumor cell induced platelet aggregation in vitro comprising, as a single unit for administration to the tumor cells, compounds in a synergistic admixture:
   (a) a 1,4-dihydropyridine calcium channel blocker; and
   (b) a prostacyclin, wherein each of the compounds alone inhibit tumor cell induced platelet aggregation in vitro in a first amount, wherein the composition contains a second amount of each compound less than the first amount such that each compound when administered in vitro alone inhibits less than 20% tumor cell induced platelet aggregation in vivo and wherein the composition inhibits aggregation induced in vitro by a tumor cell selected from B16 amelanotic melanoma, 3LL Lewis Lung carcinoma and Walter 256 carcinosarcoma.

2. The composition of claim 1 wherein the 1,4- dihydropyridine is selected from the group consisting of nifedipine and nimodipine.

3. The composition of claim 1 wherein the prostacyclin is prostaglandin PGI2.

4. The composition of claim 1 consisting essentially of prostacyclin prostaglandin PGI2 in combination with the 1,4-dihydropyridine calcium channel blocker selected from the group consisting of nifidipine and nimodipine.

5. A method for inhibiting tumor cell induced platelet aggregation which comprises administering to a mixture of tumor cells and platelets in solution in vitro a tumor cell and platelet aggregation inhibiting amount of a composition including compounds in a synergistic admixture
   (a) a 1,4-dihydropyridine calcium channel blocker; and
   (b) a prostacyclin or a stimulating agent for the prostacyclin, wherein each of the compounds alone inhibit tumor cell induced platelet aggregation in vitro in a first amount, wherein the composition contains a second amount of each compound less than the first amount which when administered in vitro alone produces less than 20% tumor cell induced platelet aggregation in vivo and which does not significantly inhibit platelet aggregation alone, wherein the composition inhibits aggregation induced in vitro by a tumor cell selected from B16 amelanotic melanoma, 3LL Lewis Lung carcinoma and Walker 256 carcinosarcoma.

6. The method of claim 5 wherein the 1,4-dihydropyrdine is selected from the group consisting of nifedipine or nimodipine.

7. The method of claim 5 wherein the prostacyclin is prostaglandin PGI2.

8. The method of claim 5 wherein the composition consists essentially of the prostacyclin prostaglandin PGI2 in combination with a 1,4-dihydropyridine calcium channel blocker selected from the group consisting of nifedipine and nimodipine.

* * * * *

UNITED STATES PATENT AND TRADEMARK OFFICE
CERTIFICATE OF CORRECTION

Page 1 of 3

PATENT NO. : 4,950,680
DATED : August 21, 1990
INVENTOR(S) : John D. Taylor and Kenneth V. Honn It is certified that error appears in the above—identified patent and that said Letters Patent is hereby corrected as shown below:

Column 1, line 33, --stimulating agents-- should be inserted after "prostacyclin".

Column 2, line 67, --of-- should be inserted before "phosphatidic".

Column 4, line 17, "metabolities" should be --metabolites--.

Column 5, line 30, after "prostacyclin" a semicolon -- ; -- should be inserted.

Column 5, line 50, "diphenylaklylamines" should be --diphenylalkylamines--.

Column 6, line 22, "auxiliary" should be --axillary--.

Column 8, line 44, "(15mM0)" should be --(15mM)--.

UNITED STATES PATENT AND TRADEMARK OFFICE
CERTIFICATE OF CORRECTION

PATENT NO. : 4,950,680
DATED : August 21, 1990
INVENTOR(S) : John D. Taylor and Kenneth V. Honn It is certified that error appears in the above-identified patent and that said Letters Patent is hereby corrected as shown below:

Column 8, line 49, "mg/ml Neomycin sulfate" should be --1 mg/ml Neomycin sulfate--.

Column 9, line 47, "he" should be --the--.

Column 12, line 1, after "lines", the "U;" should be deleted.

Column 12, line 25, "100 uM" should be --10 uM--.

Column 12, line 40, (footnote 4), --Control-- should be inserted before "Light".

Column 12, line 41, "(TXB$^2$)" should be --(TXB$_2$)--.

Column 12, line 41, (footnote 5), --Control-- should be inserted before "(TXB$_2$)".

Column 12, line 43, --mg-- should be inserted after "2.83".

Column 12, line 47, "Uk" should be --UK--.

Column 12, line 49, "Uk" should be --UK--.

UNITED STATES PATENT AND TRADEMARK OFFICE
CERTIFICATE OF CORRECTION

PATENT NO. : 4,950,680

DATED : August 21, 1990

INVENTOR(S) : John D. Taylor and Kenneth V. Honn

It is certified that error appears in the above—identified patent and that said Letters Patent is hereby corrected as shown below:

Column 12, line 54, "Uk" should be --UK--.

Column 12, line 58, "Uk" should be --UK--.

Column 14, line 10, "$3\pm 1 \times 108$" should be --$3\pm 1 \times 10^8$--.

Column 15, line 19, "along" should be --alone--.

Column 16, line 15, "thrombine" should be --thrombin--.

Column 17, line 47, "phosphodieserase" should be --phosphodiesterase--.

Column 17, line 54, "ehnace" should be --enhance--.

Column 18, line 25 (Claim 1), "Walter" should be --Walker--.

Column 18, line 58 (Claim 6), "dihydropyrdine" should be --dihydropyridine--.

Signed and Sealed this

Seventh Day of July, 1992

*Attest:*

DOUGLAS B. COMER

*Attesting Officer*     Acting Commissioner of Patents and Trademarks